US005824875A

United States Patent [19]

Ranu

[11] Patent Number: 5,824,875
[45] Date of Patent: Oct. 20, 1998

[54] 1-AMINOCYCLOPROPANE-1-CARBOXYLATE SYNTHASE GENES FROM PELARGONIUM

[75] Inventor: Rajinder S. Ranu, Fort Collins, Colo.

[73] Assignee: Colorado State University through its agent Colorado State University Research Foundation, Fort Collins, Colo.

[21] Appl. No.: 724,194

[22] Filed: Oct. 1, 1996

[51] Int. Cl.$^6$ ............................. A01H 5/00; C12N 15/82; C12N 15/63; C07H 21/04
[52] U.S. Cl. ...................... 800/205; 435/320.1; 435/419; 536/23.6; 536/24.1; 536/24.5; 800/DIG. 22
[58] Field of Search .................................. 536/23.6, 24.1, 536/24.5; 435/320.1, 419; 800/205, DIG. 22

[56] References Cited

U.S. PATENT DOCUMENTS

| | | | |
|---|---|---|---|
| 4,782,022 | 11/1988 | Puhler et al. | 435/172.3 |
| 4,962,028 | 10/1990 | Bedbrook et al. | 435/172.3 |
| 5,123,951 | 6/1992 | See et al. | 504/127 |
| 5,378,619 | 1/1995 | Rogers | 435/172.3 |
| 5,416,250 | 5/1995 | Ferro et al. | 800/205 |

OTHER PUBLICATIONS

"The Role of Ethylene in Regulating Growth of Deepwater Rice," H. Kende, S. Hoffmann–Benning and M. Sauter MSU–DOE Plant Research Laboratory, Michigan State University, East Lansing, MI, USA, J.C.Pech et al. (eds.), Cellular and Molecular Aspects of the Plant Hormone Ethylene, 329–334, 1993, Kluwer Academic Publishers.

"Temporal and Spatial Regulation of 1–Aminocyclopropane–1 Carboxylate Oxidase in the Pollination–Induced Senescence of Orchid Flowers", Jeanette A. Nadeau, Xian Sheng Zhang, Helen Nair, and Sharman D. O'Neill*, Division of Biological Science, Section of Plant Biology, University of California at Davis, Davis, CA, Plant Physiol. (1993) 103:31–9.

"A Flower Senescence–Related mRNA from Carnation Shares Sequence Similarity with Fruit Ripening–Related mRNAs Involved in Ethylene Biosynthesis," Hong Wang and William R. Woodson, Department of Horticulture, Purdue University, West Lafayette, IN, Plant Physiol (1991) 1000–1001.

"Ethylene and Flower Senescence," Michael S. Reid & Men–Jen Wu, Department of Environmental Horticulture, University of California, Davis, CA, Plant Growth Regulation II: 37–43, 1992.

"Cloning and Characterization of the cDNA encoding 1–Aminocyclopropane–1–Carboxylate (ACC) Synthase from Pelargonium Hortorum–sincerity", Jianguo Fan, Dong Wang and Rajinder Ranu, Department of Plant Pathology and Weed Science, Colorado State University, Fort Collins, RNA 2368, The FASEB Journal, Apr. 30, 1996, vol. 10, No. 6.

"Expression of Two ACC Synthase mRNAs In Carnation Flower Parts During Aging and Following Treatment With Ethylene," Hans Henskens, Dianne Somhorst and Ernest J. Woltering, Agrotechnological Research Institute (ATO–DLO) P.O. Box 17, 6700 AA Wageningen, The Netherlands, J.C. Pech et al. (eds), Cellular and Molecular Aspects of the Plant Hormone Ethylene, 323–324, 1993 Kluwer Academic Publishers.

"Genes Involved in Ethylene Biogenesis," Ethylene In Plant Biology, Second Edition, Frederick B. Abeles, Page W. Morgan, Mikal E. Saltveit, Jr., Academic Press, Inc. Harcourt Brace Jovanovich, Publishers, pp. 251–252.

"Introduction and Historical Perspectives", Ethylene In Plant Biology, Second Edition, Frederick B. Abeles, Page W. Morgan, Mikal E. Saltveit, Jr., Academic Press, Inc. Harcourt Brace Jovanovich, Publishers, pp. 1–13.

"The Biosynthesis of Ethylene," Ethylene In Plant Biology, Second Edition, Frederick B. Abeles, Page W. Morgan, Mikal E. Saltveit, Jr., Academic Press, Inc. Harcourt Brace Jovanovich, Publishers, pp. 26–55.

"Roles and Physiological Effects of Ethylene in Plant Physiology," Ethylene In Plant Biology, Second Edition, Frederick B. Abeles, Page W. Morgan, Mikal E. Saltveit, Jr., Academic Press, Inc., Harcourt Brace Jovanovich, Publishers, pp. 176–181.

"Nucleotide Sequence Of A cDNA Encoding 1–Aminocyclopropane–1–Carboxylate Oxidase from Senescing Orchid Petals," Jeanette A. Nadeau and Sharman D. O'Neill, Division of Biological Science, Section of Plant Biology, University of California, Davis, CA., Plant Physiol, (1995) 108:833–834.

"Nucleotide Sequence of a cDNA Encoding the Ethylene–Forming Enzyme from Petunia Corollas," Hong Wang and William R. Woodson, Department of Horticulture, Purdue University, West Lafayette, IN, Plant Physiol, (1992) 100, 535–536.

"A Revised Medium For Rapid Growth and Bio Assays With Tobacco Tissue Cultures," Toshio Murashige and Folke Skoog, Physiologia Plantarum, vol. XV, 1962 ed., Societas Physiologiae Plantarum Scandinavica, Ejnar Munksgaard, Copenhagen.

(List continued on next page.)

Primary Examiner—Elizabeth F. McElwain
Assistant Examiner—Thanda Wai
Attorney, Agent, or Firm—Luke Santangelo

[57] ABSTRACT

Genes which encode ACC synthase are identified for the geranium plant, specifically *Pelargonium x hortorum* cv sincerity. These genes are shown as modified to achieve a transgenic plant which resists wilting and the like as a result of reduced ethylene production. This alteration is reproduced by the transformed plant. Isolation of high quality mRNA is achieved through use and adaptation of a 2-butoxyethanol precipitation technique using large amount of initial tissue in order to achieve critical mass for precipitation.

25 Claims, 9 Drawing Sheets

OTHER PUBLICATIONS

Van der Straeten et al. Cloning and sequence of two different cDNAs encoding 1–aminocyclopropane–1–carboxylate synthase in tomato. PNAS USA. 87:4859–4863, Jun. 1990.

Nakajima et al. Molecular cloning and sequence of a complementary DNA encoding 1–aminocyclopropane–1–carboxylate synthase induced by tissue wounding. Plant Cell Physiology. 31(7):1021–1029 Sep. 1990.

Sato et al. The 1–aminocyclopropane–1–carboxylate synthase of Cucurbita. The Journal of Biological Chemistry. 266(6):3752–3759, Feb. 1992.

Botella et al. Identification and characterization of a full–length cDNA encoding for an auxin–induced 1–aminocyclopropane–1–carboxylate synthase from etiolated mung bean hypocotyl segments and expression of its mRNA response to indole–3–acetic acid. Pl, Nov. 1992.

Liang et al. The 1–aminocyclopropane–1–carboxylate synthase gene family of *Arabidopsis thaliana*. PNAS USA. 89:11046–11050, Nov. 1992.

Bailey et al. Nucleotide sequence of the *Nicotiana tabacum* cv Xanthi gene encoding 1–aminocyclopropane–1–carboxylate synthase. Plant Physiology. 100:1615–1616, Nov. 1992.

Abeles, F.B., et. al. 1992, *Ethylene in Plant Biology*. Eds. Abeles, F.B., Morgan, P.W. and Saltveit, M.E. Academic Press, New York, pp. 285–291 and 1–13.

Yang, S. F., et al, 1984, "Ethylene Biosynthesis and its Regulation in Higher Plants", *Annu. Rev Plant Physiol.* 35:155–189.

Nell, T.A., 1993, "Use and Care Advice" White J.W., ed., Geranium IV. *The Grower's Manual*, Edition Four, Ball Publishing, Geneva, IL pp. 171–172.

Chomczynski, P., et al, 1987, "Single–Step Method of RNA Isolation by Acid Guanidinium Thiocyanate–Phenol–Chloroform Extraction", *Analytical Biochemistry*, 162, 156–159.

Manning, K., 1991, "Isolation of Nucleic Acids from Plants by Differential Solvent Precipitation", *Analytical Biochemistry* 195, 45–50.

Mullis, K.B., et al, 1987, "Specific Synthesis of DNA in Vitro via a Polymerase–Catalyzed Chain Reaction", *Methods in Enzymology*, 155:355–350.

Sanger, F., et al, 1977, "DNA sequencing with chain–terminating inhibitors", *Proc. Natl. Acad. Sci. USA* 74:5463–5467.

Ranu, R.S., 1995, "DNA Sequencing with ▲ Taq® Polymerase", *Biotechniques* 18:390–395.

Ranu, R.S., et al, 1996, "In Vitro Translation of the Full–Length RNA Transcript of Figwort Mosaic Virus (Caulimovirus)", *Gene Expression*, vol. 5:143–153.

Ranu, R.S., et al, 1979, "Regulation of Protein Synthesis in Rabbit Reticulocyte Lysates: Preparation of Efficient Protein Synthesis Lysates andthe Purification and Characterization of the Heme–Regulated Translational Inhibitory Protein Kinase", *Methods in Enzymology* vol. 60:459–484.

Rottmann, W.H., et al, 1991, 1–Aminocyclopropane–1–Carboxylate Synthase in Tomato is Encoded by a Multigene Family Whose Transcription is Induced During Furit and Floral Senescence, *Journal of Molecular Biology*, 222, 937–961.

Van Der Straeten, D., et al, 1990, "Cloning and sequence of two different cDNAs encoding 1–aminocyclopropane–1–carboxylate synthase in tomato", *Proceeding of the National Academy of Sciences*, 87:4859–4863.

Zarembinski, T.I., et al, 1994, "Ethylene biosynthesis and action: a case of conservation", *Plant Molecular Biology*, 26:1579–1597.

Park, K.Y., et al, 1992, "Molecular cloning of an 1–aminocyclopropane–1–carboxylate synthase from senescing carnation flower petals", *Plant Molecular Biology*, 18:377–386.

Schlagnhaufer, C.D., et al, 1995, "Molecular cloning of an ozone–induced 1–aminocyclopropane–1–carboxylate synthase cDNA and its relationship with a loss of rbcS in potato (*Solanum tuberosum* L.)", *Plant Molecular Biology*, 28:93–103.

Wang, T.W. and Arteca, R.N., 1995, "Identification and Characterization of cDNAs Encoding Ethylene Biosynthetic Enzymes from Pelargonium x hortorum cv Snow Mass Leaves", *Plant Physiology*, 109:627–636.

Sato, T., et al, 1989, "Cloning the mRNA encoding 1–aminocyclopropane–1–carboxylate synthase, the key enzyme for ethylene biosynthesis in plants", *Proceedings of the National Academy of Sciences*, 86:6621–6625.

Nakajima, N., et al, 1990, "Molecular Cloning and Sequence of a Complementary DNA Encoding 1–Aminocyclopropane–1–carboxylate Synthase Induced by Tissue Wounding", *Plant Cell Physiology*, 31:1021–1029.

Dong, J.G., et al, 1991, "Cloning of a cDNA encoding 1–aminocyclopropane–1–carboxylate synthase and expression of its mRNA in ripening apple fruit", *Planta*, 185:38–45.

Olson, D.C., et al, 1991, "Differential expression of two genes for 1–aminocyclopropane–1–carboxylate synthase in tomato fruits", *Proceedings of National Academy of Sciences*, 88:5340–5344.

Smith, C.J.S., et al, 1991, "Antisense RNA inhibition of polygalacturonase gene expression in transgenic tomatoes", *Nature*, 334:724–726.

Yip, W.K., et al, 1990, "Differential accumulation of transcripts for four tomato 1–aminocyclopropane–1–carboxylate synthase homologs under various conditions", *Proceedings of the National Academy of Sciences*, 89:2475–2479.

Botella, J.R., et al, 1992, "Identification and characterization of a full–length cDNA encoding for an auxin–induced 1–aminocyclopropane–1–carboxylate synthase from etiolated mung bean hypocotyl segments and expression of its mRNA in reponse to indole–3–acetic acid", *Plant Molecular Biology*, 20:425–436.

Liang, X., et al, 1992, "The 1–aminocyclopropane–1–carboxylate synthase gene family of *Arabidopsis thaliana*", *Proceedings of the National Academy of Sciences*, 89:11046–11050.

Oeller, P.W., et al, "Reversible Inhibition of Tomato Fruit Senescence by Antisense RNA", *Science*, 254:437–439.

John, M.E., "An efficient method for isolation of RNA and DNA from plants containing polyphenolics", Nucleic Acids Research 20:2381, 1992.

Logemann, J., et al, 1987, "Improved Method for the Isolation of RNA from Plant Tissues", Anal Biochem 163: 16–20.

Kende, H., et al, 1993, "Ethylene Biosynthesis", *Annual Review of Plant Physiology, Plant Mol. Biol.*, 44:283–307.

Murray, A.J. 1993, "Expression of EFE Antisense RNA in Tomato Causes Retardation of Leaf Senescense and Most Fruit Ripening Characteristics", *Cellular and Molecular Aspects of the Plant Hormone Ethylene*, 327–328.

Michael, M.Z., et al, 1993, "Cloning of Ethylene Biosynthetic Genes Involved in Petal Senescence of Carnation and Petunia, and their Antisense Expression in Transgenic Plants", *Cellular and Molecular Aspects of the Plant Hormone Ethylene*, 298–303.

Gray, J.E., et al, 1993, "Altered Gene Expression, Leaf Senescence, and Fruit Ripening by Inhibiting Ethylene Synthesis with EFE–Antisense Genes", *Cellular and Molecular Aspects of the Plant Hormone Ethylene*, 82–89.

Theologis, A., et al 1993, "Modifying Fruit Ripening By Supressing Gene Expression", *Cellular and Molecular Aspects of the Plant Hormone Ethylene*, 19–23.

Hamilton, AJ et al 1990, "Antisense Gene that Inhibits Synthesis of the Hormone Ethylene in Transgenic Plants", *Nature*, 346:284–287.

E–mail message dated Apr. 22, 1998 from GenBank User Services re:release date of U17229.

Plasmid pPHSacc41
[SEQ ID NO:1]

GAATTCGGCACGAGCTCGCTTCTGAGTGCCTAATTATTTTTGTCCAAGCTCTCAGTACGT
ACGTGTTGTACGTGTTTACATAGATGGAGAACAAGAGCAAACAGCTTCTGTCAAAGATTG
CAACCAACGACGGACACGGCGAGAACTCCCCATATTTCGATGGTTGGAAGGCTTATGACC
GTGATCCGTTCCATCCGTCTCAGAATCCTAACGGTGTTATCCAGATGGGTTTAGCTGAAA
ATCAGCTTTCATCTGACTTGATTGAAGATTGGGTGAGGTCCAACCCAGAAGCCTCAATCT
GCACTCTTGAGGGAGTTGGTAAGTTCAAGGACGTAGCTAACTTTCAGGACTACCATGGCC
TGCTGGAGTTCAGGCACGCCGTGGCTAAATTTATGAGCAGAGGAAGGGGCGGGAAGGTCA
CATTTGATCCCGACCGTGTCGTCATGAGCGGCGGACCGACCGGAGCCAACGAGCTCATCG
TCTTCTGTTTGGCCAATCCCGGCGACGCTTTCCTTCTCCATCTCCTTATTATCCAGCAA
ACGACCGTGACTTGCAGTGGCGAACCGGAGCTCAGATCATTCCGGTGCACTGCAACAGCT
CCAACGGTTTCAAGATAACCAGAGAGGCACTAGAAAGATCATACGCACAAGCACAAGAAA
GCAACATAAACGTAAAAGGCGTGCTCTTAACCAACCCATCGAACCCTCTAGGCACAATTC
TGGACCGCGACACTCTCAAGAGCATCGTCAGCTTCGTCACCGACAACAACATCCACCTAG
TCATCGACGAAATCTACGCCGCCACCGTTTTCGCCGCCCCGGAGTTCGTAAGCGTCTCCG
AAATCCTCCAAGAAATGGACGACACCACGTGCAACCCCGACCTCATCCACATCGTGTACA
GCCTGTCCAAGGACTTGGGCATGCCCGGGTTCCGCGTCGGGATCGTGTACTCATTCAACG
ACGACGTCGTATCCTGCGCACGGAAGATGTCGAGCTTCGGGTTGGTGTCGACCCAGACGC
AGCACCTTCTCGCAGCGATGCTATCCGACGACGTTTTCGTGGAGCGGTTCCTCGCGGAGA
GCCGGAGCTTGGGGAGGAGGCACGGCGTGTTCACGAAAGGGCTCGAGGAGTTGGGGATTG
GGTGTTTAAAGAGCAACGCGGGGCTCTACTTCTGGATGGATTTGCGGAAGCTTCTAGAAG
AAGAGACGTTTGAGGCGGAGATGGTGCTGTGGAAGGTGATTATTAATGAGGTGAAGCTAA
ACGTGTCTCCGGGGTCGTCGTTTCATTGCGTGGAGCCGGGTTGGTTTAGGGTTTGCTTTG
CCAACATGGACGACGAGACGGTCCACGTGGCGCTGAAGAGGATCAGGGCGTTTGTGAGGA
AGAAGGAGGTGGGTCCGGTGAAGAGGAAGAGGTTCATGGACAACCTTAACCTCAGGCTGA
GCTTCTCGTCGCTAAGGTACGATGAGAGTGTGATGTTGTCGCCGCACATAATGGTGTCCC
CGCACTCGCCGCTTGTTCGTGCGAGAACATAATGAGCATGCACGTTTTTATTTGCTACTG
TTAGTAATTAACTAATTAATTGTTATTTGATTGTGTGCTGAATGTTGGATTCTTTCTTTG
TAGAAGTGAAGTATAGGAGATGTTTTTAACCAATTACCGTAGATATATATGCAGTGGAAT
TAAGAAAAATAAGAGGTTAAATATTAATTCCATGCATATATATGTAGGAAGGAATTGGTA
CATATTTTAGGGTTTGCTGATGTTTTCTTTCATCATGAATTGGTACATATTTATGATGTT
CAAGGCTCCAAGTGATGGATACATGGAGGATTCATTTGGATGCATGCCTTGCAAGAGTCA
GCAATCTTTGTTAATTAGTGTATGGTTTGTGATAATAAAGATGCAAAATTCTGTGTTGTT
TTATTACTAAAAAAAAAAAAAAAAA

FIG. 3 pPHSacc44

[SEQ NO:2]

GAATTCGGCACGAGTACGTGTTGTACGTGTTTACATAGATGGAGAACAAGAGCAAACAGCTT
CTGTCAAAGATTGCAACCAACGACGGACACGGCGAGAACTCCCCATATTTCGATGGTTGGAA
GGCTTATGACCGTGATCCGTTCCATCCGTCTCAGAATCCTAACGGTGTTATCCAGATGGGTT
TAGCTGAAAATCAGCTTTCATCTGACTTGATTGAAGATTGGGTGAGGTCCAACCCAGAAGCC
TCAATCTGCACTCTAGAGGGAGTTGGTAAGTTCAAGGACGTAGCTAACTTTCAGGACTACCA
TGGCCTGCTGGAGTTCAGGCACGCCGTGGCTAAATTTATGAGCAGAGGAAGGGGCGGGAAGG
TCACATTTGATCCCGACCGTGTCGTCATGAGCGGCGGACCGACCGGAGCCAACGAGCTCATC
GTCTTCTGTTTGGCCAATCCCGGCGACGCTTTCCTTCTCCCATCTCCTTATTATCCAGGAAA
CGACCGTGACTTGCAGTGGCGAACCGGAGCTCAGATCATTCCGGTGCACTGCAACAGCTCCA
ACGGTTTCAAGATAACCAGAGAGGCCCTAGAAAGATCATACGCACAAGCACAAGAAAGCAAC
ATAAACGTAAAAGGCGTGCTCTTAACCAACCCATCGAACCCTCTAGGCACAATTCTGGACCG
CGACACTCTCAAGAGCATCGTCAGCTTCGTCACCGACAACAACATCCACCTAGTCATCGACG
AAATCTACGCCGCCACCGTTTTCGCCGCCCCGGAGTTCGTAAGCGTCTCCGAAATCCTCCAA
GAAATGGACGACACCACGTGCAACCCCGACCTCATCCACATCGTGTACAGCCTGTCCAAGGA
CTTGGGCATGCCCGGGTTCCGCGTCGGGATCGTGTACTCATTCAACGACGACGTCGTATCCT
GCGCACGGAAGATGTCGAGCTTCGGGTTGGTGTCGACCCAGACGCAGCACCTTCTCGCAGCG
ATGCTATCCGACGACGTTTTCGTGGAGCGGTTCCTCGCGGAGAGCCGGAGCTTGGGGAGGAG
GCACGGCGTGTTCACGAAAGGGCTCGAGGAGTTGGGGATTGGGTGTTTAAAGAGCAACGCGG
GGCTCTACTTCTGGATGGATTTGCGGAAGCTTCTAGAAGAAGAGACGTTTGAGGCGGAGATG
GTGCTGTGGAAGGTGATTATTAATGAGGTGAAGCTAAACGTGTCTCCGGGGTCGTCGTTTCA
TTGCGTGGAGCCGGGTTGGTTTAGGGTTTGCTTTGCCAACATGGACGACGAGACGGTCCACG
TGGCGCTGAAGAGGATCAGGGCGTTTGTGGGGAAGAAGGAGGTGGGTCCGGTGAAGAGGAAG
AGGTTCATGGACAACCTTAACCTCAGGCTGAGCTTCTCGTCGCTAAGGTACGATGAGAGTGT
GATGTTGTCGCCGCACATAATGGTGTCCCCGCACTCGCCGCTTGTTCGTGCGAGAACATAAT
GAGCATGCACGTTTTTTTTGCTACTGTTAGTAATTAACTAATTAATTGTTATTTGATTGTG
TGCTGAATGTTGGATTCTTTCTTTGTAGAAGTGAAGTATAGGAGATGTTTTTAACCAATTAC
CGTAGATATATATGCAGTGGAATTAAGAAAAATAAGAGGTTAAATATTAATTCCATGCATAT
ATATGTAGGAAGGAATTGGTACATATTTTAGGGTTTGCTGATGTTTTCTTTCATCATGAATT
GGTACATATTTATGATGTTCAAGGCTCCAAGTGATGGATACATGGAGGATTCATTTGGATGC
ATGCCTTGCAAGAGTCAGCAATCTTTGTTAATTAGTGTATGGTTTGTGATAATAAAGATGCA
AAATTCTGTGTTGTTTAAAAAAAAAAAAAAAAAAACTCGAGCAAATTGGAACCACCTTT
CGATCCTTATGCAAACTCAATTAACTACCTCTTGGCTGCTTATTACATCCCTTATGTGGGAC
TTAATGGTTACGTTGGTACCACTCCAAATCTTACCCGTACGGATTATAAAGATTGGTGGCA

Figure 4

GGACTGTTAGCTGTAGAGGGCGGACAGATGCTGATGCTGTTGTAAGAGCGTTCTGAGCGAGC
GCGTTCAAGGTGTGAGCCGTACAATAAGACGGTGCTTACTTCACGGCGGCGATCTCGAAGCT
GAGAAACAACCTTGGTCAAAATGGGATCAAAGATGAAGGGATATGGGTTCCCAAGTGCTTGA
GCTGAGAATCGGACCCATAGTAACGTCTTATCGGCCGATCCCAACTCGTTGGGTACTCTAGG
ATGCCACCGGAGATATTGAGTATAATGTATACTACCGGAAATGAAAGTACGGCCCGGTGGCT
TCTTTCCCAAGGGTGCAAACGGCAAGATTGCTAGGTCTTATCTATTGACGAATAAATAATGT
TTAATTTGAGTGTGCAAATAACAATCCAATAAGTTCGGAACTACTGGTTACATATTGCGTTG
GTACATACTAGCTAACGTCTATGGGACTGAGTGGTTTGTGTAGTTTCAAACATTATTATGAG
CTCGAGGTTGTATGATGGGAAATGTATTATATATGAAAGTTATTAATCAATTATAATGTATA
CCGCTATATTCTTTTATGTAACTCTTATGAAATAAAGCAATAGTTCATAAAAAAAAAAAAA
AAAAAAAAAAA

Figure 4a pPHSacc49
[SEQ ID NO:3]

```
GAATTCGGCACGAGCTTCACAGCACAGCTCTTTAAGCAACCATCATCATCTTTTG
CATATTAATTCTGAGGATTTTCTTTGAGCAAAACAACATCGATCAAAAATGGTGA
ACATGTCCTCAACAACTAACCAAAGAACATTGTTATCTAAGATGGCAACTGGAGA
TGGACATGGCGAAAACTCACCTTACTTTGATGGCTGGAAAGCTTACGACAACAAT
CCTTTCCATCTCACCCAAAACCCTCAAGGTGTCATCCAGATGGGCCTCGCAGAAA
ATCAGCTTTCTTTCGAGTTGATTGAGCAATGGGTCCTTAACAACCCACAAGCCTC
CATTTGCACAGCACAAGGTCTGCAAGAATTCAAGGACACTGCAATCTTTCAAGAT
TACCATGGCTTGCAGAGTTCAGATATGCTGTTTGCAAATTTCATGGGAAAGGTGA
GAGGAAACAGAGTAACATTTAACCCAGATCGCATAGTTATGAGTGGAGGAGCAAC
TGGAGCTCATGAAATGATTGCCTTCTGTTTGGCTGATCCTGGCGATGCTTTTCTT
GTCCCAACTCCTTATTATCCTGGATTTGATAGAGACCTGAGGTGGAGAACTGGTG
TGCAGCTAATTCCTGTAGTAGTCTGTGAAAGTGAAAACAATTTCAGGATCACCCG
AAGTGCCTTAGAAGAAGCCTATGAGAGAGCTCAAGAGGACAAGATTAGAGTGAAG
GGATTGCTCATAACAAACCCATCAAACCCACTAGGAACTATCCTGGACAGAGAGA
CACTAGTCAGTCTAGTGAGCTTCATCAATGAAAAGAACATTCACTTGGTCTGTGA
TGAAATCTACGCCGCCACAGTCTTCTCTCAGCCCGCTTTCGTTAGCATTGCTGAG
GTTATCGAGCAAGAGAACGTTTCGTGCAACCGCGACCTCATCCACATTGTCTACA
GCCTGTCCAAGGACATGGGCTTCCCTGGCTTCAGGGTGGGGATTGTCTACTCCTA
CAATGACGCAGTTGTGAATTGTGCGCGAAAGATGTCAAGTTTCGGCCTTGTATCC
ACACAAACTCAGCACCTAATCGCATCAATGCTCTCGGACGATGAATTCGTGGACA
CATTCATCGTGGAGAGCGCGAAGAGGCTAGCGAGAAGGTACACAACCTTCACAAG
AGGGCTTGCACAAGTGAACATTGGATGCCTAAAGAGCAATGGGGGGTTATTCATA
TGGATGGACTTGAGGAGGCTTCTCAAGGAGAAGACTTTCGAGGCGGAGATGGCTC
TGTGGAGAGTGATAATCAATGAAGTGAAGCTAAATGTGTCGCCAGGGGCGTCGTT
CCATTGCTCGGAGCCAGGGTGGTTTAGAGTGTGCTTTGCCAACATGGATGACTTG
ACGATGCAGGTGGCTCTGAGGAGGATCATAACATTTGCACTTCAGAACAAGGAAG
CTGCGGTTTTGCCTGCAATCAAGAGACAGTGTTGGCAAAACAACCTTGGAAGGCT
CAGCTTGTCTTTCAGGAGATTTGATGATTTCACGATGTCTCCAATGTCCCCTCAC
TCCCCAATACAATCACCACTTGTGAGAGCCACTTAGAAACACATGAATAATAGAG
AATAACGGGCGATGCGGCCGCCAAAAATAGGTTGATCTATGTATGCATTAACGTT
TTTAGTTAATCTGTGTTTAATAGTATAACAAGAAGGAACAAAATGTATTCTTTCT
GTATAAATAACCCGGGGTAGGTTGATCTATGTATGCATTAACGTTTTTAGTTAAT
CTGTGTTTATATGTATAACAAGAAGGAACAAAATGTATTCTTTCTGTATAAATAA
CCCAAACTTAGAAGATGCTTGCTGTGCATCCTTCTGGGAAAAAAAAAAAAAAAA
AAAAAAA
```

FIG. 5

Deduced Amino Acid Sequence encoded by pPHSacc41

[SEQ ID NO:4]

MENKSKQLLSKIATNDGHGENSPYFDGWKAYDRDPFHPSQNPNGVIQMGL
AENQLSSDLIEDWVRSNPEASICTLEGVGKFKDVANFQDYHGLLEFRHAV
AKFMSRGRGGKVTFDPDRVVMSGGPTGANELIVFCLANPGDAFLLPSPYY
PANDRDLQWRTGAQIIPVHCNSSNGFKITREALERSYAQAQESNINVKGV
LLTNPSNPLGTILDRDTLKSIVSFVTDNNIHLVIDEIYAATVFAAPEFVS
VSEILQEMDDTTCNPDLIHIVYSLSKDLGMPGFRVGIVYSFNDDVVSCAR
KMSSFGLVSTQTQHLLAAMLSDDVFVERFLAESRSLGRRHGVFTKGLEEL
GIGCLKSNAGLYFWMDLRKLLEEETFEAEMVLWKVIINEVKLNVSPGSSF
HCVEPGWFRVCFANMDDETVHVALKRIRAFVRKKEVGPVKRKRFMDNLNL
RLSFSSLRYDESVMLSPHIMVSPHSPLVRART

FIG. 6

Deduced Amino Acid Sequence encoded by pPHSacc44

[SEQ ID NO:5]

MENKSKQLLSKIATNDGHGENSPYFDGWKAYDRDPFHPSQNPNGVIQMGLAENQLSSDLI
EDWVRSNPEASICTLEGVGKFKDVANFQDYHGLLEFRHAVAKFMSRGRGGKVTFDPDRVV
MSGGPTGANELIVFCLANPGDAFLLPSPYYPGNDRDLQWRTGAQIIPVHCNSSNGFKITR
EALERSYAQAQESNINVKGVLLTNPSNPLGTILDRDTLKSIVSFVTDNNIHLVIDEIYAA
TVFAAPEFVSVSEILQEMDDTTCNPDLIHIVYSLSKDLGMPGFRVGIVYSFNDDVVSCAR
KMSSFGLVSTQTQHLLAAMLSDDVFVERFLAESRSLGRRHGVFTKGLEELGIGCLKSNAG
LYFWMDLRKLLEEETFEAEMVLWKVIINEVKLNVSPGSSFHCVEPGWFRVCFANMDDETV
HVALKRIRAFVGKKEVGPVKRKRFMDNLNLRLSFSSLRYDESVMLSPHIMVSPHSPLVRA
RT

FIG. 7

Deduced Amino Acid Sequence encoded by pPHSacc49

[SEQ ID NO:6]

MVNMSSTTNQRTLLSKMATGDGHGENSPYFDGWKAYDNNPFHLTQNPQGVIQMGL
AENQLSFELIEQWVLNNPQASICTAQGLQEFKDTAIFQDYHGLQSSDMLFANFMG
KVRGNRVTFNPDRIVMSGGATGAHEMIAFCLADPGDAFLVPTPYYPGFDRDLRWR
TGVQLIPVVVCESENNFRITRSALEEAYERAQEDKIRVKGLLITNPSNPLGTILD
RETLVSLVSFINEKNIHLVCDEIYAATVFSQPAFVSIAEVIEQENVSCNRDLIHI
VYSLSKDMGFPGFRVGIVYSYNDAVVNCARKMSSFGLVSTQTQHLIASMLSDDEF
VDTFIVESAKRLARRYTTFTRGLAQVNIGCLKSNGGLFIWMDLRRLLKEKTFEAE
MALWRVIINEVKLNVSPGASFHCSEPGWFRVCFANMDDLTMQVALRRIITFALQN
KEAAVLPAIKRQCWQNNLGRLSLSFRRFDDFTMSPMSPHSPIQSPLVRAT

FIG. 8

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 1945 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:1:

| | | | | | | |
|---|---|---|---|---|---|---|
| GAATTCGGCA | CGAGCTCGCT | TCTGAGTGCC | TAATTATTTT | TGTCCAAGCT | CTCAGTACGT | 60 |
| ACGTGTTGTA | CGTGTTTACA | TAGATGGAGA | ACAAGAGCAA | ACAGCTTCTG | TCAAAGATTG | 120 |
| CAACCAACGA | CGGACACGGC | GAGAACTCCC | CATATTTCGA | TGGTTGGAAG | GCTTATGACC | 180 |
| GTGATCCGTT | CCATCCGTCT | CAGAATCCTA | ACGGTGTTAT | CCAGATGGGT | TTAGCTGAAA | 240 |
| ATCAGCTTTC | ATCTGACTTG | ATTGAAGATT | GGGTGAGGTC | CAACCCAGAA | GCCTCAATCT | 300 |
| GCACTCTTGA | GGGAGTTGGT | AAGTTCAAGG | ACGTAGCTAA | CTTTCAGGAC | TACCATGGCC | 360 |
| TGCTGGAGTT | CAGGCACGCC | GTGGCTAAAT | TTATGAGCAG | AGGAAGGGGC | GGGAAGGTCA | 420 |
| CATTTGATCC | CGACCGTGTC | GTCATGAGCG | GCGGACCGAC | CGGAGCCAAC | GAGCTCATCG | 480 |
| TCTTCTGTTT | GGCCAATCCC | GGCGACGCTT | TCCTTCTCCC | ATCTCCTTAT | TATCCAGCAA | 540 |
| ACGACCGTGA | CTTGCAGTGG | CGAACCGGAG | CTCAGATCAT | TCCGGTGCAC | TGCAACAGCT | 600 |
| CCAACGGTTT | CAAGATAACC | AGAGAGGCAC | TAGAAAGATC | ATACGCACAA | GCACAAGAAA | 660 |
| GCAACATAAA | CGTAAAAGGC | GTGCTCTTAA | CCAACCCATC | GAACCCTCTA | GGCACAATTC | 720 |
| TGGACCGCGA | CACTCTCAAG | AGCATCGTCA | GCTTCGTCAC | CGACAACAAC | ATCCACCTAG | 780 |

| | | | | | |
|---|---|---|---|---|---|
| TCATCGACGA | AATCTACGCC | GCCACCGTTT | TCGCCGCCCC | GGAGTTCGTA | AGCGTCTCCG | 840
| AAATCCTCCA | AGAAATGGAC | GACACCACGT | GCAACCCCGA | CCTCATCCAC | ATCGTGTACA | 900
| GCCTGTCCAA | GGACTTGGGC | ATGCCCGGGT | TCCGCGTCGG | GATCGTGTAC | TCATTCAACG | 960
| ACGACGTCGT | ATCCTGCGCA | CGGAAGATGT | CGAGCTTCGG | GTTGGTGTCG | ACCCAGACGC | 1020
| AGCACCTTCT | CGCAGCGATG | CTATCCGACG | ACGTTTTCGT | GGAGCGGTTC | CTCGCGGAGA | 1080
| GCCGGAGCTT | GGGGAGGAGG | CACGGCGTGT | TCACGAAAGG | GCTCGAGGAG | TTGGGGATTG | 1140
| GGTGTTTAAA | GAGCAACGCG | GGGCTCTACT | TCTGGATGGA | TTTGCGGAAG | CTTCTAGAAG | 1200
| AAGAGACGTT | TGAGGCGGAG | ATGGTGCTGT | GGAAGGTGAT | TATTAATGAG | GTGAAGCTAA | 1260
| ACGTGTCTCC | GGGGTCGTCG | TTTCATTGCG | TGGAGCCGGG | TTGGTTTAGG | GTTTGCTTTG | 1320
| CCAACATGGA | CGACGAGACG | GTCCACGTGG | CGCTGAAGAG | GATCAGGGCG | TTTGTGAGGA | 1380
| AGAAGGAGGT | GGGTCCGGTG | AAGAGGAAGA | GGTTCATGGA | CAACCTTAAC | CTCAGGCTGA | 1440
| GCTTCTCGTC | GCTAAGGTAC | GATGAGAGTG | TGATGTTGTC | GCCGCACATA | ATGGTGTCCC | 1500
| CGCACTCGCC | GCTTGTTCGT | GCGAGAACAT | AATGAGCATG | CACGTTTTA | TTTGCTACTG | 1560
| TTAGTAATTA | ACTAATTAAT | TGTTATTTGA | TTGTGTGCTG | AATGTTGGAT | TCTTTCTTTG | 1620
| TAGAAGTGAA | GTATAGGAGA | TGTTTTTAAC | CAATTACCGT | AGATATATAT | GCAGTGGAAT | 1680
| TAAGAAAAAT | AAGAGGTTAA | ATATTAATTC | CATGCATATA | TATGTAGGAA | GGAATTGGTA | 1740
| CATATTTTAG | GGTTTGCTGA | TGTTTTCTTT | CATCATGAAT | TGGTACATAT | TTATGATGTT | 1800
| CAAGGCTCCA | AGTGATGGAT | ACATGGAGGA | TTCATTTGGA | TGCATGCCTT | GCAAGAGTCA | 1860
| GCAATCTTTG | TTAATTAGTG | TATGGTTTGT | GATAATAAAG | ATGCAAAATT | CTGTGTTGTT | 1920
| TTATTACTAA | AAAAAAAAA | AAAAA | | | | 1945

( 2 ) INFORMATION FOR SEQ ID NO:2:

( i ) SEQUENCE CHARACTERISTICS:
    ( A ) LENGTH: 2678 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:2:

| | | | | | |
|---|---|---|---|---|---|
| GAATTCGGCA | CGAGTACGTG | TTGTACGTGT | TTACATAGAT | GGAGAACAAG | AGCAAACAGC | 60
| TTCTGTCAAA | GATTGCAACC | AACGACGGAC | ACGGCGAGAA | CTCCCCATAT | TTCGATGGTT | 120
| GGAAGGCTTA | TGACCGTGAT | CCGTTCCATC | CGTCTCAGAA | TCCTAACGGT | GTTATCCAGA | 180
| TGGGTTTAGC | TGAAAATCAG | CTTTCATCTG | ACTTGATTGA | AGATTGGGTG | AGGTCCAACC | 240
| CAGAAGCCTC | AATCTGCACT | CTAGAGGGAG | TTGGTAAGTT | CAAGGACGTA | GCTAACTTTC | 300
| AGGACTACCA | TGGCCTGCTG | GAGTTCAGGC | ACGCCGTGGC | TAAATTTATG | AGCAGAGGAA | 360
| GGGGCGGGAA | GGTCACATTT | GATCCCGACC | GTGTCGTCAT | GAGCGGCGGA | CCGACCGGAG | 420
| CCAACGAGCT | CATCGTCTTC | TGTTTGGCCA | ATCCCGGCGA | CGCTTTCCTT | CTCCCATCTC | 480
| CTTATTATCC | AGGAAACGAC | CGTGACTTGC | AGTGGCGAAC | CGGAGCTCAG | ATCATTCCGG | 540
| TGCACTGCAA | CAGCTCCAAC | GGTTTCAAGA | TAACCAGAGA | GGCCCTAGAA | AGATCATACG | 600
| CACAAGCACA | AGAAAGCAAC | ATAAACGTAA | AAGGCGTGCT | CTTAACCAAC | CCATCGAACC | 660
| CTCTAGGCAC | AATTCTGGAC | CGCGACACTC | TCAAGAGCAT | CGTCAGCTTC | GTCACCGACA | 720
| ACAACATCCA | CCTAGTCATC | GACGAAATCT | ACGCCGCCAC | CGTTTTCGCC | GCCCCGGAGT | 780

| | | | | | | |
|---|---|---|---|---|---|---|
| TCGTAAGCGT | CTCCGAAATC | CTCCAAGAAA | TGGACGACAC | CACGTGCAAC | CCCGACCTCA | 840 |
| TCCACATCGT | GTACAGCCTG | TCCAAGGACT | TGGGCATGCC | CGGGTTCCGC | GTCGGGATCG | 900 |
| TGTACTCATT | CAACGACGAC | GTCGTATCCT | GCGCACGGAA | GATGTCGAGC | TTCGGGTTGG | 960 |
| TGTCGACCCA | GACGCAGCAC | CTTCTCGCAG | CGATGCTATC | CGACGACGTT | TTCGTGGAGC | 1020 |
| GGTTCCTCGC | GGAGAGCCGG | AGCTTGGGGA | GGAGGCACGG | CGTGTTCACG | AAAGGGCTCG | 1080 |
| AGGAGTTGGG | GATTGGGTGT | TAAAGAGCA | ACGCGGGGCT | CTACTTCTGG | ATGGATTTGC | 1140 |
| GGAAGCTTCT | AGAAGAAGAG | ACGTTGAGG | CGGAGATGGT | GCTGTGGAAG | GTGATTATTA | 1200 |
| ATGAGGTGAA | GCTAAACGTG | TCTCCGGGGT | CGTCGTTTCA | TTGCGTGGAG | CCGGGTTGGT | 1260 |
| TTAGGGTTTG | CTTTGCCAAC | ATGGACGACG | AGACGGTCCA | CGTGGCGCTG | AAGAGGATCA | 1320 |
| GGGCGTTTGT | GGGGAAGAAG | GAGGTGGGTC | CGGTGAAGAG | GAAGAGGTTC | ATGGACAACC | 1380 |
| TTAACCTCAG | GCTGAGCTTC | TCGTCGCTAA | GGTACGATGA | GAGTGTGATG | TTGTCGCCGC | 1440 |
| ACATAATGGT | GTCCCCGCAC | TCGCCGCTTG | TTCGTGCGAG | AACATAATGA | GCATGCACGT | 1500 |
| TTTTTTTTGC | TACTGTTAGT | AATTAACTAA | TTAATTGTTA | TTTGATTGTG | TGCTGAATGT | 1560 |
| TGGATTCTTT | CTTTGTAGAA | GTGAAGTATA | GGAGATGTTT | TAACCAATT | ACCGTAGATA | 1620 |
| TATATGCAGT | GGAATTAAGA | AAAATAAGAG | GTTAAATATT | AATTCCATGC | ATATATATGT | 1680 |
| AGGAAGGAAT | TGGTACATAT | TTTAGGGTTT | GCTGATGTTT | TCTTTCATCA | TGAATTGGTA | 1740 |
| CATATTTATG | ATGTTCAAGG | CTCCAAGTGA | TGGATACATG | GAGGATTCAT | TTGGATGCAT | 1800 |
| GCCTTGCAAG | AGTCAGCAAT | CTTTGTTAAT | TAGTGTATGG | TTTGTGATAA | TAAAGATGCA | 1860 |
| AAATTCTGTG | TTGTTTAAAA | AAAAAAAAA | AAAAAAACT | CGAGCAAATT | GGAACCACCT | 1920 |
| TTCGATCCTT | ATGCAAACTC | AATTAACTAC | CTCTTGGCTG | CTTATTACAT | CCCTTATGTG | 1980 |
| GGACTTAATG | GTTACGTTGG | TACCACTCCA | AATCTTACCC | GTACGGATTA | TAAAAGATTG | 2040 |
| GTGGCAGGAC | TGTTAGCTGT | AGAGGGCGGA | CAGATGCTGA | TGCTGTTGTA | AGAGCGTTCT | 2100 |
| GAGCGAGCGC | GTTCAAGGTG | TGAGCCGTAC | AATAAGACGG | TGCTTACTTC | ACGGCGGCGA | 2160 |
| TCTCGAAGCT | GAGAAACAAC | CTTGGTCAAA | ATGGGATCAA | AGATGAAGGG | ATATGGGTTC | 2220 |
| CCAAGTGCTT | GAGCTGAGAA | TCGGACCCAT | AGTAACGTCT | TATCGGCCGA | TCCCAACTCG | 2280 |
| TTGGGTACTC | TAGGATGCCA | CCGGAGATAT | TGAGTATAAT | GTATACTACC | GGAAATGAAA | 2340 |
| GTACGGCCCG | GTGGCTTCTT | TCCCAAGGGT | GCAAACGGCA | AGATTGCTAG | GTCTTATCTA | 2400 |
| TTGACGAATA | AATAATGTTT | AATTTGAGTG | TGCAAATAAC | AATCCAATAA | GTTCGGAACT | 2460 |
| ACTGGTTACA | TATTGCGTTG | GTACATACTA | GCTAACGTCT | ATGGACTGA | GTGGTTTGTG | 2520 |
| TAGTTTCAAA | CATTATTATG | AGCTCGAGGT | TGTATGATGG | GAAATGTATT | ATATATGAAA | 2580 |
| GTTATTAATC | AATTATAATG | TATACCGCTA | TATTCTTTTA | TGTAACTCTT | ATGAAATAAA | 2640 |
| GCAATAGTTC | ATAAAAAAAA | AAAAAAAAA | AAAAAAA | | | 2678 |

( 2 ) INFORMATION FOR SEQ ID NO:3:

( i ) SEQUENCE CHARACTERISTICS:
        ( A ) LENGTH: 1878 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

| | | | | | | |
|---|---|---|---|---|---|---|
| GAATTCGGCA | CGAGCTTCAC | AGCACAGCTC | TTTAAGCAAC | CATCATCATC | TTTTGCATAT | 60 |
| TAATTCTGAG | GATTTTCTTT | GAGCAAAACA | ACATCGATCA | AAAATGGTGA | ACATGTCCTC | 120 |

```
AACAACTAAC CAAAGAACAT TGTTATCTAA GATGGCAACT GGAGATGGAC ATGGCGAAAA      180
CTCACCTTAC TTTGATGGCT GGAAAGCTTA CGACAACAAT CCTTCCATC TCACCCAAAA      240
CCCTCAAGGT GTCATCCAGA TGGGCCTCGC AGAAAATCAG CTTTCTTTCG AGTTGATTGA      300
GCAATGGGTC CTTAACAACC CACAAGCCTC CATTTGCACA GCACAAGGTC TGCAAGAATT     360
CAAGGACACT GCAATCTTTC AAGATTACCA TGGCTTGCAG AGTTCAGATA TGCTGTTTGC     420
AAATTTCATG GGAAAGGTGA GAGGAAACAG AGTAACATTT AACCCAGATC GCATAGTTAT     480
GAGTGGAGGA GCAACTGGAG CTCATGAAAT GATTGCCTTC TGTTTGGCTG ATCCTGGCGA     540
TGCTTTTCTT GTCCCAACTC CTTATTATCC TGGATTTGAT AGAGACCTGA GGTGGAGAAC     600
TGGTGTGCAG CTAATTCCTG TAGTAGTCTG TGAAAGTGAA AACAATTTCA GGATCACCCG     660
AAGTGCCTTA GAAGAAGCCT ATGAGAGAGC TCAAGAGGAC AAGATTAGAG TGAAGGGATT     720
GCTCATAACA AACCCATCAA ACCCACTAGG AACTATCCTG GACAGAGAGA CACTAGTCAG     780
TCTAGTGAGC TTCATCAATG AAAAGAACAT TCACTTGGTC TGTGATGAAA TCTACGCCGC     840
CACAGTCTTC TCTCAGCCCG CTTTCGTTAG CATTGCTGAG GTTATCGAGC AAGAGAACGT     900
TTCGTGCAAC CGCGACCTCA TCCACATTGT CTACAGCCTG TCCAAGGACA TGGGCTTCCC    960
TGGCTTCAGG GTGGGGATTG TCTACTCCTA CAATGACGCA GTTGTGAATT GTGCGCGAAA   1020
GATGTCAAGT TTCGGCCTTG TATCCACACA AACTCAGCAC CTAATCGCAT CAATGCTCTC   1080
GGACGATGAA TTCGTGGACA CATTCATCGT GGAGAGCGCG AAGAGGCTAG CGAGAAGGTA   1140
CACAACCTTC ACAAGAGGGC TTGCACAAGT GAACATTGGA TGCCTAAAGA GCAATGGGGG   1200
GTTATTCATA TGGATGGACT TGAGGAGGCT TCTCAAGGAG AAGACTTTCG AGGCGGAGAT   1260
GGCTCTGTGG AGAGTGATAA TCAATGAAGT GAAGCTAAAT GTGTCGCCAG GGGCGTCGTT   1320
CCATTGCTCG GAGCCAGGGT GGTTTAGAGT GTGCTTTGCC AACATGGATG ACTTGACGAT   1380
GCAGGTGGCT CTGAGGAGGA TCATAACATT TGCACTTCAG AACAAGGAAG CTGCGGTTTT   1440
GCCTGCAATC AAGAGACAGT GTTGGCAAAA CAACCTTGGA AGGCTCAGCT TGTCTTTCAG   1500
GAGATTTGAT GATTTCACGA TGTCTCCAAT GTCCCCTCAC TCCCCAATAC AATCACCACT   1560
TGTGAGAGCC ACTTAGAAAC ACATGAATAA TAGAGAATAA CGGGCGATGC GGCCGCCAAA   1620
AATAGGTTGA TCTATGTATG CATTAACGTT TTTAGTTAAT CTGTGTTTAA TAGTATAACA   1680
AGAAGGAACA AAATGTATTC TTTCTGTATA AATAACCCGG GGTAGGTTGA TCTATGTATG   1740
CATTAACGTT TTTAGTTAAT CTGTGTTTAT ATGTATAACA AGAAGGAACA AAATGTATTC   1800
TTTCTGTATA AATAACCCAA ACTTAGAAGA TGCTTGCTGT GCATCCTTCT GGGAAAAAAA   1860
AAAAAAAAAA AAAAAAA                                                  1878
```

( 2 ) INFORMATION FOR SEQ ID NO:4:

( i ) SEQUENCE CHARACTERISTICS:
        ( A ) LENGTH: 482 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
Met Glu Asn Lys Ser Lys Gln Leu Leu Ser Lys Ile Ala Thr Asn Asp
 1               5                  10                  15

Gly His Gly Glu Asn Ser Pro Tyr Phe Asp Gly Trp Lys Ala Tyr Asp
                20                  25                  30

Arg Asp Pro Phe His Pro Ser Gln Asn Pro Asn Gly Val Ile Gln Met
            35                  40                  45
```

```
Gly  Leu  Ala  Glu  Asn  Gln  Leu  Ser  Ser  Asp  Leu  Ile  Glu  Asp  Trp  Val
     50                       55                      60

Arg  Ser  Asn  Pro  Glu  Ala  Ser  Ile  Cys  Thr  Leu  Glu  Gly  Val  Gly  Lys
65                       70                      75                           80

Phe  Lys  Asp  Val  Ala  Asn  Phe  Gln  Asp  Tyr  His  Gly  Leu  Leu  Glu  Phe
                    85                      90                           95

Arg  His  Ala  Val  Ala  Lys  Phe  Met  Ser  Arg  Gly  Arg  Gly  Gly  Lys  Val
                    100                     105                    110

Thr  Phe  Asp  Pro  Asp  Arg  Val  Val  Met  Ser  Gly  Gly  Pro  Thr  Gly  Ala
               115                     120                    125

Asn  Glu  Leu  Ile  Val  Phe  Cys  Leu  Ala  Asn  Pro  Gly  Asp  Ala  Phe  Leu
     130                     135                    140

Leu  Pro  Ser  Pro  Tyr  Tyr  Pro  Ala  Asn  Asp  Arg  Asp  Leu  Gln  Trp  Arg
145                      150                    155                          160

Thr  Gly  Ala  Gln  Ile  Ile  Pro  Val  His  Cys  Asn  Ser  Ser  Asn  Gly  Phe
                    165                     170                    175

Lys  Ile  Thr  Arg  Glu  Ala  Leu  Glu  Arg  Ser  Tyr  Ala  Gln  Ala  Gln  Glu
               180                     185                    190

Ser  Asn  Ile  Asn  Val  Lys  Gly  Val  Leu  Leu  Thr  Asn  Pro  Ser  Asn  Pro
          195                     200                    205

Leu  Gly  Thr  Ile  Leu  Asp  Arg  Asp  Thr  Leu  Lys  Ser  Ile  Val  Ser  Phe
     210                     215                    220

Val  Thr  Asp  Asn  Asn  Ile  His  Leu  Val  Ile  Asp  Glu  Ile  Tyr  Ala  Ala
225                      230                     235                         240

Thr  Val  Phe  Ala  Ala  Pro  Glu  Phe  Val  Ser  Val  Ser  Glu  Ile  Leu  Gln
                    245                     250                         255

Glu  Met  Asp  Asp  Thr  Thr  Cys  Asn  Pro  Asp  Leu  Ile  His  Ile  Val  Tyr
               260                     265                         270

Ser  Leu  Ser  Lys  Asp  Leu  Gly  Met  Pro  Gly  Phe  Arg  Val  Gly  Ile  Val
          275                     280                    285

Tyr  Ser  Phe  Asn  Asp  Asp  Val  Val  Ser  Cys  Ala  Arg  Lys  Met  Ser  Ser
     290                     295                    300

Phe  Gly  Leu  Val  Ser  Thr  Gln  Thr  Gln  His  Leu  Leu  Ala  Ala  Met  Leu
305                      310                     315                         320

Ser  Asp  Asp  Val  Phe  Val  Glu  Arg  Phe  Leu  Ala  Glu  Ser  Arg  Ser  Leu
                    325                     330                         335

Gly  Arg  Arg  His  Gly  Val  Phe  Thr  Lys  Gly  Leu  Glu  Glu  Leu  Gly  Ile
               340                     345                    350

Gly  Cys  Leu  Lys  Ser  Asn  Ala  Gly  Leu  Tyr  Phe  Trp  Met  Asp  Leu  Arg
          355                     360                    365

Lys  Leu  Leu  Glu  Glu  Glu  Thr  Phe  Glu  Ala  Glu  Met  Val  Leu  Trp  Lys
     370                     375                    380

Val  Ile  Ile  Asn  Glu  Val  Lys  Leu  Asn  Val  Ser  Pro  Gly  Ser  Ser  Phe
385                      390                     395                         400

His  Cys  Val  Glu  Pro  Gly  Trp  Phe  Arg  Val  Cys  Phe  Ala  Asn  Met  Asp
                    405                     410                         415

Asp  Glu  Thr  Val  His  Val  Ala  Leu  Lys  Arg  Ile  Arg  Ala  Phe  Val  Arg
               420                     425                    430

Lys  Lys  Glu  Val  Gly  Pro  Val  Lys  Arg  Lys  Arg  Phe  Met  Asp  Asn  Leu
          435                     440                    445

Asn  Leu  Arg  Leu  Ser  Phe  Ser  Ser  Leu  Arg  Tyr  Asp  Glu  Ser  Val  Met
450                      455                     460
```

```
Leu  Ser  Pro  His  Ile  Met  Val  Ser  Pro  His  Ser  Pro  Leu  Val  Arg  Ala
465                 470                 475                 480

Arg  Thr
```

( 2 ) INFORMATION FOR SEQ ID NO:5:

( i ) SEQUENCE CHARACTERISTICS:
        ( A ) LENGTH: 482 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

```
Met  Glu  Asn  Lys  Ser  Lys  Gln  Leu  Leu  Ser  Lys  Ile  Ala  Thr  Asn  Asp
1                   5                   10                  15

Gly  His  Gly  Glu  Asn  Ser  Pro  Tyr  Phe  Asp  Gly  Trp  Lys  Ala  Tyr  Asp
                    20                  25                  30

Arg  Asp  Pro  Phe  His  Pro  Ser  Gln  Asn  Pro  Asn  Gly  Val  Ile  Gln  Met
               35                  40                  45

Gly  Leu  Ala  Glu  Asn  Gln  Leu  Ser  Ser  Asp  Leu  Ile  Glu  Asp  Trp  Val
          50                  55                  60

Arg  Ser  Asn  Pro  Glu  Ala  Ser  Ile  Cys  Thr  Leu  Glu  Gly  Val  Gly  Lys
65                  70                  75                  80

Phe  Lys  Asp  Val  Ala  Asn  Phe  Gln  Asp  Tyr  His  Gly  Leu  Leu  Glu  Phe
                    85                  90                  95

Arg  His  Ala  Val  Ala  Lys  Phe  Met  Ser  Arg  Gly  Arg  Gly  Gly  Lys  Val
               100                 105                 110

Thr  Phe  Asp  Pro  Asp  Arg  Val  Val  Met  Ser  Gly  Gly  Pro  Thr  Gly  Ala
          115                 120                 125

Asn  Glu  Leu  Ile  Val  Phe  Cys  Leu  Ala  Asn  Pro  Gly  Asp  Ala  Phe  Leu
130                 135                 140

Leu  Pro  Ser  Pro  Tyr  Tyr  Pro  Gly  Asn  Asp  Arg  Asp  Leu  Gln  Trp  Arg
145                 150                 155                 160

Thr  Gly  Ala  Gln  Ile  Ile  Pro  Val  His  Cys  Asn  Ser  Ser  Asn  Gly  Phe
                    165                 170                 175

Lys  Ile  Thr  Arg  Glu  Ala  Leu  Glu  Arg  Ser  Tyr  Ala  Gln  Ala  Gln  Glu
               180                 185                 190

Ser  Asn  Ile  Asn  Val  Lys  Gly  Val  Leu  Leu  Thr  Asn  Pro  Ser  Asn  Pro
          195                 200                 205

Leu  Gly  Thr  Ile  Leu  Asp  Arg  Asp  Thr  Leu  Lys  Ser  Ile  Val  Ser  Phe
     210                 215                 220

Val  Thr  Asp  Asn  Asn  Ile  His  Leu  Val  Ile  Asp  Glu  Ile  Tyr  Ala  Ala
225                 230                 235                 240

Thr  Val  Phe  Ala  Ala  Pro  Glu  Phe  Val  Ser  Val  Ser  Glu  Ile  Leu  Gln
                    245                 250                 255

Glu  Met  Asp  Asp  Thr  Thr  Cys  Asn  Pro  Asp  Leu  Ile  His  Ile  Val  Tyr
               260                 265                 270

Ser  Leu  Ser  Lys  Asp  Leu  Gly  Met  Pro  Gly  Phe  Arg  Val  Gly  Ile  Val
          275                 280                 285

Tyr  Ser  Phe  Asn  Asp  Asp  Val  Val  Ser  Cys  Ala  Arg  Lys  Met  Ser  Ser
     290                 295                 300

Phe  Gly  Leu  Val  Ser  Thr  Gln  Thr  Gln  His  Leu  Leu  Ala  Ala  Met  Leu
305                 310                 315                 320

Ser  Asp  Asp  Val  Phe  Val  Glu  Arg  Phe  Leu  Ala  Glu  Ser  Arg  Ser  Leu
                    325                 330                 335
```

|     |     |     |     |     |     |     |     |     |     |     |     |     |     |
| --- | --- | --- | --- | --- | --- | --- | --- | --- | --- | --- | --- | --- | --- |
| Gly | Arg | Arg | His<br>340 | Gly | Val | Phe | Thr | Lys<br>345 | Gly | Leu | Glu | Glu<br>350 | Leu | Gly | Ile |
| Gly | Cys | Leu<br>355 | Lys | Ser | Asn | Ala | Gly<br>360 | Leu | Tyr | Phe | Trp<br>365 | Met | Asp | Leu | Arg |
| Lys | Leu<br>370 | Leu | Glu | Glu | Glu | Thr<br>375 | Phe | Glu | Ala | Glu | Met<br>380 | Val | Leu | Trp | Lys |
| Val<br>385 | Ile | Ile | Asn | Glu | Val<br>390 | Lys | Leu | Asn | Val | Ser<br>395 | Pro | Gly | Ser | Ser | Phe<br>400 |
| His | Cys | Val | Glu | Pro<br>405 | Gly | Trp | Phe | Arg | Val<br>410 | Cys | Phe | Ala | Asn | Met<br>415 | Asp |
| Asp | Glu | Thr | Val<br>420 | His | Val | Ala | Leu | Lys<br>425 | Arg | Ile | Arg | Ala | Phe<br>430 | Val | Gly |
| Lys | Lys | Glu<br>435 | Val | Gly | Pro | Val | Lys<br>440 | Arg | Lys | Arg | Phe | Met<br>445 | Asp | Asn | Leu |
| Asn | Leu<br>450 | Arg | Leu | Ser | Phe | Ser<br>455 | Ser | Leu | Arg | Tyr | Asp<br>460 | Glu | Ser | Val | Met |
| Leu<br>465 | Ser | Pro | His | Ile | Met<br>470 | Val | Ser | Pro | His | Ser<br>475 | Pro | Leu | Val | Arg | Ala<br>480 |
| Arg | Thr |  |  |  |  |  |  |  |  |  |  |  |  |  |  |

( 2 ) INFORMATION FOR SEQ ID NO:6:

( i ) SEQUENCE CHARACTERISTICS:
( A ) LENGTH: 490 amino acids
( B ) TYPE: amino acid
( C ) STRANDEDNESS: single
( D ) TOPOLOGY: linear ( x i ) SEQUENCE DESCRIPTION: SEQ ID NO:6:

|     |     |     |     |     |     |     |     |     |     |     |     |     |     |     |     |
| --- | --- | --- | --- | --- | --- | --- | --- | --- | --- | --- | --- | --- | --- | --- | --- |
| Met<br>1 | Val | Asn | Met | Ser<br>5 | Ser | Thr | Thr | Asn | Gln<br>10 | Arg | Thr | Leu | Leu | Ser<br>15 | Lys |
| Met | Ala | Thr | Gly<br>20 | Asp | Gly | His | Gly | Glu<br>25 | Asn | Ser | Pro | Tyr | Phe<br>30 | Asp | Gly |
| Trp | Lys | Ala<br>35 | Tyr | Asp | Asn | Asn | Pro<br>40 | Phe | His | Leu | Thr | Gln<br>45 | Asn | Pro | Gln |
| Gly | Val<br>50 | Ile | Gln | Met | Gly | Leu<br>55 | Ala | Glu | Asn | Gln | Leu<br>60 | Ser | Phe | Glu | Leu |
| Ile<br>65 | Glu | Gln | Trp | Val | Leu<br>70 | Asn | Asn | Pro | Gln | Ala<br>75 | Ser | Ile | Cys | Thr | Ala<br>80 |
| Gln | Gly | Leu | Gln | Glu<br>85 | Phe | Lys | Asp | Thr | Ala<br>90 | Ile | Phe | Gln | Asp | Tyr<br>95 | His |
| Gly | Leu | Gln | Ser | Ser<br>100 | Asp | Met | Leu | Phe | Ala<br>105 | Asn | Phe | Met | Gly | Lys<br>110 | Val |
| Arg | Gly | Asn | Arg<br>115 | Val | Thr | Phe | Asn | Pro<br>120 | Asp | Arg | Ile | Val | Met<br>125 | Ser | Gly |
| Gly | Ala | Thr<br>130 | Gly | Ala | His | Glu | Met<br>135 | Ile | Ala | Phe | Cys | Leu<br>140 | Ala | Asp | Pro |
| Gly | Asp | Ala | Phe | Leu<br>145 | Val | Pro | Thr<br>150 | Pro | Tyr | Tyr | Pro<br>155 | Gly | Phe | Asp | Arg<br>160 |
| Asp | Leu | Arg | Trp | Arg<br>165 | Thr | Gly | Val | Gln<br>170 | Leu | Ile | Pro | Val | Val<br>175 | Val | Cys |
| Glu | Ser | Glu | Asn<br>180 | Asn | Phe | Arg | Ile<br>185 | Thr | Arg | Ser | Ala | Leu<br>190 | Glu | Glu | Ala |
| Tyr | Glu | Arg<br>195 | Ala | Gln | Glu | Asp<br>200 | Lys | Ile | Arg | Val | Lys<br>205 | Gly | Leu | Leu | Ile |

| | | | | | | | | | | | | | | |
|---|---|---|---|---|---|---|---|---|---|---|---|---|---|---|
| Thr | Asn 210 | Pro | Ser | Asn | Pro 215 | Leu | Gly | Thr | Ile | Leu 220 | Asp | Arg | Glu | Thr | Leu |
| Val 225 | Ser | Leu | Val | Ser | Phe 230 | Ile | Asn | Glu | Lys | Asn 235 | Ile | His | Leu | Val | Cys 240 |
| Asp | Glu | Ile | Tyr | Ala 245 | Ala | Thr | Val | Phe | Ser 250 | Gln | Pro | Ala | Phe | Val 255 | Ser |
| Ile | Ala | Glu | Val 260 | Ile | Glu | Gln | Glu | Asn 265 | Val | Ser | Cys | Asn | Arg 270 | Asp | Leu |
| Ile | His | Ile 275 | Val | Tyr | Ser | Leu | Ser 280 | Lys | Asp | Met | Gly | Phe 285 | Pro | Gly | Phe |
| Arg | Val 290 | Gly | Ile | Val | Tyr | Ser 295 | Tyr | Asn | Asp | Ala | Val 300 | Val | Asn | Cys | Ala |
| Arg 305 | Lys | Met | Ser | Ser | Phe 310 | Gly | Leu | Val | Ser | Thr 315 | Gln | Thr | Gln | His | Leu 320 |
| Ile | Ala | Ser | Met | Leu 325 | Ser | Asp | Asp | Glu | Phe 330 | Val | Asp | Thr | Phe | Ile 335 | Val |
| Glu | Ser | Ala | Lys 340 | Arg | Leu | Ala | Arg | Arg 345 | Tyr | Thr | Thr | Phe | Thr 350 | Arg | Gly |
| Leu | Ala | Gln 355 | Val | Asn | Ile | Gly | Cys 360 | Leu | Lys | Ser | Asn | Gly 365 | Gly | Leu | Phe |
| Ile | Trp 370 | Met | Asp | Leu | Arg | Arg 375 | Leu | Leu | Lys | Glu | Lys 380 | Thr | Phe | Glu | Ala |
| Glu 385 | Met | Ala | Leu | Trp | Arg 390 | Val | Ile | Ile | Asn | Glu 395 | Val | Lys | Leu | Asn | Val 400 |
| Ser | Pro | Gly | Ala | Ser 405 | Phe | His | Cys | Ser | Glu 410 | Pro | Gly | Trp | Phe | Arg 415 | Val |
| Cys | Phe | Ala | Asn 420 | Met | Asp | Asp | Leu | Thr 425 | Met | Gln | Val | Ala | Leu 430 | Arg | Arg |
| Ile | Ile | Thr 435 | Phe | Ala | Leu | Gln | Asn 440 | Lys | Glu | Ala | Ala | Val 445 | Leu | Pro | Ala |
| Ile | Lys 450 | Arg | Gln | Cys | Trp | Gln 455 | Asn | Asn | Leu | Gly | Arg 460 | Leu | Ser | Leu | Ser |
| Phe 465 | Arg | Arg | Phe | Asp | Asp 470 | Phe | Thr | Met | Ser | Pro 475 | Met | Ser | Pro | His | Ser 480 |
| Pro | Ile | Gln | Ser | Pro 485 | Leu | Val | Arg | Ala | Thr 490 | | | | | | |

( 2 ) INFORMATION FOR SEQ ID NO:7:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GAGAGAGAGA GAGAGAGAGA ACTAGTCTCG AGTTTTTTTT TTTTTTTTTT      50

( 2 ) INFORMATION FOR SEQ ID NO:8:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:8:

AATTCGGCAG AG      12

( 2 ) INFORMATION FOR SEQ ID NO:9:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i x ) FEATURE:
    ( A ) NAME/KEY: misc_feature
    ( B ) LOCATION: group(3, 6, 9, 12, 18, 21)
    ( D ) OTHER INFORMATION: /note= "N represents Inosine"

( x i ) SEQUENCE DESCRIPTION: SEQ ID NO:9:

GGNYTNCCNG GNTTYMGNRT NGG   23

( 2 ) INFORMATION FOR SEQ ID NO:10:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i x ) FEATURE:
    ( A ) NAME/KEY: misc_feature
    ( B ) LOCATION: group(3, 5, 6, 15, 18)
    ( D ) OTHER INFORMATION: /note= "N represents Inosine"

( x i ) SEQUENCE DESCRIPTION: SEQ ID NO:10:

CANANNCKRA ASMANCCNRS YTC   23

( 2 ) INFORMATION FOR SEQ ID NO:11:

( i ) SEQUENCE CHARACTERISTICS:
    ( A ) LENGTH: 35 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:11:

Asn Val Ser Pro Gly Ser Ser Phe Leu Cys Ser Glu Pro Gly Trp Phe
1     5       10       15

Arg Val Cys Phe Ala Asn Met Asp Asn Ala Thr Leu Asp Val Ala Leu
    20       25       30

Asn Arg Ile
  35

( 2 ) INFORMATION FOR SEQ ID NO:12:

( i ) SEQUENCE CHARACTERISTICS:
    ( A ) LENGTH: 33 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:12:

Tyr Phe Asp Gly Trp Lys Ala Tyr Asp Arg Asp Pro Tyr His Ser Thr
1     5       10       15

Lys Asn Ser Asn Gly Val Ile Gln Met Gly Leu Ala Glu Asn Gln Leu
    20       25       30

Cys (2) INFORMATION FOR SEQ ID NO:13:

(i) SEQUENCE CHARACTERISTICS:
  (A) LENGTH: 38 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:13:

Tyr Ser Leu Ser Lys Asp Met Gly Met Pro Gly Phe Arg Val Gly Ile
1               5                   10                  15

Ile Tyr Ser Tyr Asn Asp Arg Val Val Ser Thr Ala Arg Arg Met Ser
            20                  25                  30

Ser Phe Gly Leu Val Ser
        35

1-AMINOCYCLOPROPANE-1-CARBOXYLATE SYNTHASE GENES FROM PELARGONIUM

BACKGROUND OF THE INVENTION

This invention relates to the field of compositions and methods for inhibiting the enzyme 1-aminocyclopropane-1-carboxylate (ACC) synthase in geranium thereby prolonging the shelf-life of cut flowers as well as reducing leaf yellowing and petal abscission during shipping and storage.

A variety of factors cause wilting and natural abscission in flowers, particularly after a cutting of the plant or when flowers have been removed from the plant. Such factors include increased oxygen levels, wounding, chemical stress, and the plant's own production of ethylene. Of these factors, the plant's production of ethylene, has been shown to play a key role in natural senescence, the degenerative process which generally leads to controlled cell death in plants, but also in the degradation of flowers after they have been cut.

Ethylene, in all higher plants, is important to plant growth and development from seed germination, seedling growth to flowering and senescence (Abeles, F. B. et al. (1992), In: *Ethylene in Plant Biology*. Eds. Abeles, F. B. et al., Academic Press, New York, pp 285–291 and 1–13; Yang, S. F. et al. (1984), *Annu. Rev Plant Physiol*: 35, 155–189). Ethylene production in plants can also be associated with trauma induced by mechanical wounding, chemicals, stress (such as produced by temperature and water amount variations), and by disease. Hormones can also stimulate ethylene production. Such ethylene, also sometimes called "stress ethylene", can be an important factor in storage effectiveness for plants. Moreover, exposure of plant tissue to a small amount of ethylene often may be associated with increased production of ethylene by other adjacent plants. This autocatalytic effect may be often associated with losses in marketability of plant material during storage and transportation (Abeles et al., supra; Yang et al., supra).

The ethylene biosynthetic pathway in plants was established by Adams and Yang (Adams D. O., et al., (1979) *Proc. Nat'l Acad Sci USA* 76: 170–174)). The first step involves the formation of S-adenosyl-L-methionine (AdoMet) from methionine by S-adenosyl-L-methionine synthetase. AdoMet is then converted into 1-aminocyclopropane-1-carboxylate (ACC), the direct precursor of ethylene in higher plants. This conversion is catalyzed by ACC synthase (S-adenosyl-L-methionine methyl thioadenosine-lyase, EC4.4.1.14), the rate limiting step in the ethylene biosynthetic pathway. (See also Kionka C., et al., (1984) Planta 162: 226–235; Amrhein N. et al., (1981) *Naturwissenschaften* 68: 619–620; Hoffman N. E., et al., (1982) Biochem Biophys Res Commun 104: 765–770).

Knowledge of the biosynthetic pathway for ethylene formation has been fundamental in developing strategies for inhibiting ethylene production in plants. One approach has been to use chemical inhibitors to inhibit the synthesis or activity of ethylene, two of the most common being aminoethoxyvinylglycine and aminooxyacetic acid (Rando, R. R., 1974, Science, 185, 320–324 and in Ethylene in Plant Biology, (Abeles, F. B., et al., eds. Academic Press, p. 285)]. However, chemical methods find limited use because such methods are expensive and the beneficial effect they provide is generally only short-lived.

A second approach has been to overexpress ACC deaminase, an enzyme which metabolizes ACC, thereby eliminating an intermediate in the biosynthesis of ethylene (Klee, et al., (1991) Cell 3: 1187–1193) (See also Theologis, A., et al. (1993), Cellular and Molecular Aspects of the Plant Hormone Ethylene, p. 19–23). Because ACC deaminase is a bacterial enzyme, it is heterologous, and thus, external to the plant. Thus, it is unlikely that this approach will yield a modification that will be stable from generation to generation.

Yet another approach involves attempts to genetically inhibit the production of the enzymes involved in the biosynthesis of ethylene or to inhibit the biosynthesis of the enzymes directly. This approach has the advantage of not only altering the way the plant itself functions irrespective of external factors but also of presenting a system which reproduces itself, that is, the altered plant's progeny will have the same altered properties for generations to come.

Initial efforts to better understand the enzymes which catalyze the reactions in the biosynthesis of ethylene have involved the identification and characterization of the genes encoding for AdoMet synthetase, ACC synthase, and ACC oxidase (See also Kende H., 1993, Annu Rev Plant Physiol Mol Biol 44: 283–307). Some of the genes encoding for ACC synthase have been identified for a number of plants. For instance, ACC synthase sequences have been identified for zucchini (Sato T., et al., (1989) *Proc. Natl Acad Sci USA* 86: 66216–625), winter squash (Nakajima, N., et al., (1990) *Plant Cell Physiol* 31: 1021–1029), tomato (Van Der Straeten, D., et al., (1990) *Proc Natl Acad Sci USA* 87: 4859–4863); (Rottmann, W. H., et al., (1991) *J Mol Biol* 222: 937–961), apple (Dong, J. G., et al., (1991) Planta 185: 38–45), mung bean (Botella, J. R., et al., (1992a) *Plant Mol Biol* 20: 425–436; Botella, J. R., et al., (1993) Gene 123: 249–253; Botella, J. R., et al., (1992b) *Plant Mol Biol* 18: 793–797); Kim, W. T., et al., (1992) *Plant Physiol* 98: 465–471), carnation (Park, K. Y., et al., (1992) *Plant Mol. Biol.*, 18, 377–386), *Arabidopsis thaliana* (Liang, X., et al., (1992) *Proc Natl Acad Sci USA* 89: 11046–11050; Van Der Straeten, D., et al., (1992) *Proc Natl Acad Sci USA* 89: 9969–9973), tobacco (Bailey, B. A., et al., (1992) *Plant Physiol* 100: 1615–1616), rice (Zarembinski, T. I., et al., (1993) *Mol Biol Cell* 4: 363–373), mustard (Wen, C. M., et al., (1993) *Plant Physiol* 103: 1019–1020), orchid (O'Neill, S. D., et al., (1993) Plant Cell 5: 419–432), broccoli (Pogson, B. J., et al., (1995) *Plant Physiol* 108: 651–657), and potato (Schlagnhaufer, C. D., e al. (1995) *Plant Mol. Biol.* 28: 93–103).

That ACC synthase is involved in the ethylene pathway is confirmed by the fact that increased levels of ACC synthase mRNA correlate with an increased activity of ACC synthase in plants during fruit ripening and flower senescence. Similar correlation is also observed in response to exogenous signals caused either by wounding or due to treatment with hormones such as auxin, cytokinin and ethylene. Interestingly, the expression of different classes of ACC synthase occurs from a variety of signals in a many plants, e.g. four different ACC synthase genes have been shown to be differentially expressed in tomato fruit, cell cultures, and hypocotyls during ripening, wounding, and auxin treatment (Olson, D. C., et al (1991) Proc. Natl. Acad. Sci. USA 88: 5340–5344; and Yip, W. K., (1992) Proc. Natl. Acad. Sci. USA 89: 2475–2479). Differential expression of two ACC synthase genes has also been observed in winter squash during wounding or by auxin (Nakajima, et al. (1990) Plant Cell Physiol, 31; 1021–29 and (1991) Plant Cell Physiol, 32; 1153–63). Similar differential regulation of expression ACC synthase genes takes place in carnation flowers by wounding or during senescence (Park, K. Y., et al., (1992) *Plant Mol. Biol.*, 18, 377–386). The evolution of ACC synthase genes into a multigene family that responds differentially during plant development or in response to stimuli external to the plant (Rottmann, W. H., et al., (1991) *J Mol Biol* 222: 937–961) may be a reflection of the importance of ethylene in plants. (See also Slater, A., et al., (1985) Plant Mol Biol 5: 137–147). (Smith, C. J. S., et al., (1986) Planta 168; 94–100 and Smith, C. J. S., et al. (1988) Nature 334; 724–26). (Hamilton, A. J., et al., (1990) Nature 346: 284–286; Köck, M., et al., (1991) Plant Mol Biol 17: 141–142).

The discovery of the foregoing and of other properties has lead to an understanding that it may be desirable to attempt to genetically alter the production of ethylene in plants. This approach, however, may be considered in some ways delicate. Elimination of ethylene is not a desired result as in many instances it will kill the plant. Modulation of ethylene—at the appropriate times—is the critical goal, not elimination of it entirely. This has been attempted at at least two points in the pathway: the production of ACC by ACC synthase, and the oxidation of ACC by a different enzyme, ACC oxidase. Because the ACC synthase approach can permit stable modulation and not only total elimination of ethylene, it is a preferred technique. To date, however, successful reduction of the production of ethylene through an alteration at the ACC synthase step in the pathway has only been accomplished in one plant, tomato(Oeller, et al. (1991) *Science* 254: 437–39). In spite of the seemingly simple conceptual nature of this goal, the actual accomplishment of an alteration of the ethylene biosynthetic pathway through the ACC synthase technique has remained elusive. This is particularly true for the geranium plant, perhaps due to the fact that the identification of full length genes can be difficult for plants. As discussed later, this may, in part, be due to the fact that isolation of full length or high quality RNA has been deemed "notoriously difficult" for plants. (John, M. E., Nucleic Acids Research 20: 2381, 1992, and Logemann, J. et al, Anal Biochem 163, 16–20, 1987).

Efforts by others highlight some of the difficulty involved. Recently, Arteca's laboratory (Wang, T. W. et al., (1995) *Plant Physiol.* 109: 627–636) studied two cDNA molecules encoding ACC synthase from a white flower variety of a flowering geranium plant (*Pelargonium x hortorum* cv Snow Mass Leaves). As their publication explained (perhaps after the fact), these researchers tried to identify and characterize two clones, GAC-1 and GAC-2. In spite of their efforts, they were only able to completely identify one of those cDNA gene sequences, GAC-1. Their study examined the expression of these ACC synthase genes in different plant parts of the geranium and in response to stress induced by osmotic changes (sorbitol) or metal ions ($CuCl_2$). It also evaluated the effects of ethylene on auxin 2,4-D induction in geranium leaves. The study indicated that GAC-1 expression was induced only by stress, whereas expression of GAC-2 appeared to be developmentally regulated. Furthermore, these authors speculated about possible future "transfer of antisense GAC-1, GAC-2. . . into Pelargonium tissues through the Agrobacterium transformation or particle bombardment." This confirms a desire in the art for an ACC synthase approach to altering ethylene production in such plants. In spite of this desire, however, the isolation and identification of some, if not all, the ACC synthase gene sequences—for geranium remained elusive.

Although several plant ACC synthase genes have been identified and sequenced, the current invention describes ACC synthase gene sequences which were previously unknown and which are not believed to have been easily discoverable. As mentioned, one factor which may have militated against an expectation of successfully cloning a plant gene is the particular difficulty in obtaining high-quality and full-length RNA from plants. Indeed, this process has been characterized as "notoriously difficult" by at least more than one practitioner of the art (John, M. E., *Nucleic Acids Res.* 20: 2381, 1992 and Logemann, J., et al, *Anal Biochem* 163, 16–20, 1987)). While this proved to be true for the present inventor, these difficulties were overcome by assessing a new approach to the RNA isolation process. The current inventor, after finding traditional RNA isolation methods to be ineffective, was forced to develop a non-traditional approach described herein. Basically, even though those of ordinary skill in the art had long desired to identify some gene to manipulate to alter the production of ethylene in some plants, in this case, they failed to realize that the problem lay in the need for a better isolation process. Even though the implementing technology for this process had long been available, those in the art apparently failed to realize how to use that technology to achieve the results now described. To some extent they simply may not have defined the problem, preventing the achievement the goals sought. Their efforts may properly be characterized as having taught away from the direction taken by the present inventor and, thus, the results achieve here should be considered unexpected.

Difficulties in isolating full-length mRNA in this specific case are also further reflected by the fact that one of the sequences isolated by the current inventor (clone pPHSacc49), though it may bear some similarity to portions of the clone termed GAC-2 by Wang et al., supra, (which, in any case, may have been discovered after the making of the present invention) is actually considerably longer than GAC-2. This highlights the difficulty in successfully isolating a full-length mRNA molecule using standard RNA isolation procedures in certain plant materials. Furthermore, the current inventor has isolated a third novel full-length clone (pPHSacc44). Moreover, the high quality RNA (as defined below) isolated by the current inventor is further evidenced by the fact that full length cDNA clones were obtained, and all of them could be successfully expressed in an in vitro expression system. In each case, full length ACC synthase (enzyme) protein is synthesized in vitro. In contrast, even later publications by Arteca's group do not describe the actual in vitro expression of any of the isolated DNA clones. In fact the cDNA for the GAC-2 gene was never isolated. Rather, only a partial sequence was merely deduced from the sequence of genomic clones.

This is significant because it highlights the difficulty in isolating and thereby identifying full length ACC synthase genes. Those of ordinary skill in the art had faced the same challenge. Derivation of DNA encoding ACC synthase from a genomic clone rarely is successful, and therefore, simply would not provide a reasonable expectation of success to one of ordinary skill. Only by utilizing a new and different approach did the present invention successfully identify not only one but several full length ACC synthase gene sequences from the geranium plant. Basically, it was this high quality library containing full length cDNA clones which allowed the present inventor to successfully achieve direct cloning of ACC synthase cDNA. The prior art did not discover these sequences because it could not have: the genes did not exist in the available libraries. It was this new approach which overcame the problems faced, but not solved, by others and resulted in the extraordinary successes described herein. The extraordinary success of the present invention—a nearly one hundred fold increase in positive identifications—is a consequence of the new technique for RNA isolation and cDNA identification, and not the result of analogous knowledge gained from the efforts of others. Mere comparison to other genes in the same or different plants did not and could not have yielded the successes described here. The existence of the cDNAs of interest in the library was the governing factor. Thus, even with a viable identification process, successful identification of the several geranium ACC synthase genes, let alone the actual alteration of the plant itself by means of this knowledge, would not have been likely.

Additionally, it should be understood that knowledge of full length sequence of a gene from other plants simply does not necessarily lead one to the sequences of the homologous genes in the geranium plant. First, as mentioned earlier, the genes encoding ACC synthase have evolved into a multi-gene system. There appears to be no single gene, but rather a family of genes in most cases. Thus, knowledge of one gene in one plant species is not certain to lead to one (or several) homologous or analogous genes in another plant species. Second, because known ACC synthase genes are typically so diverse in their nucleotide sequences, knowledge of one would not lead a person of ordinary skill in the art to an expectation of success in isolating the ACC synthase gene from geranium.

Antisense technology is a well known approach to creating a plant that produces less of a selected protein. Through this technology, a plant is altered by introducing a foreign DNA sequence that encodes an mRNA product complementary to part or all of the plant's "sense" mRNA encoding the protein. The presence of antisense RNA inhibits RNA function within a cell (and whole organism). Antisense RNA can bind in a highly specific manner to its complementary sense RNA resulting in blockade in processing and/or translation of the sense mRNA. Antisense RNA may also disrupt interactions between sense mRNA and sequence-specific RNA binding proteins. Antisense technology may be employed to inhibit the synthesis of an enzyme involved in ethylene biosynthesis. The genes identified by the current inventor and disclosed herein have been used for the conception of antisense sequences specific for ACC synthase mRNA. Introduction of DNA encoding such antisense RNA sequences into a geranium plant results in a plant which stably produces less ethylene.

The incorporation of antisense RNA in plants as a means to inhibit the synthesis of enzymes has been described by various investigators. Rothstein, et al. (1987) *Proc. Natl. Acad. Sci. U.S.A.* 84: 8439, found that antisense RNA inhibited nopaline synthase (nos) in tobacco. Smith, C. J. S., et al. (1988) *Nature* 334: 724, reported that antisense RNA inhibited polygalacturonase in tomato. Others have used antisense RNA to inhibit the synthesis of enzymes involved in ethylene formation. Oeller, P. W., et al., (1991) *Science* 254: 437–439, expressed RNA antisense to ACC synthase in tomato plants. Others have expressed antisense RNA to a different ethylene forming enzyme (EFE), ACC oxidase, in carnation and tomato (Michael, M. Z., et al., 1993, In: Pech, J. C., et al., eds., *Cellular and Molecular Aspects of the Plant Hormone Ethylene* (Kluwer Academic Publishers, pp. 298–302); Hamilton, A. J., et al. (1990) *Nature* 346: 284–287; Gray, et al. (1993), in Pech, J. C., et al., supra, pp. 82–89; Murray, A. J., et al. (1993) in Pech, J. C., et al., supra, pp. 327–328). The above work with antisense RNA may also be applicable to efforts to stably incorporate the sequences identified by the current inventor and their antisense sequences into geranium plants. Similarly, the success in expressing antisense RNA for ACC synthase in tomato plants may also be applicable (Oeller, et al., supra). It is noteworthy, and perhaps surprising, that neither of the foregoing disclosures have led to the long sought goal of stably altering ethylene production in geranium plants. Hence, an altered geranium plant expressing reduced levels of ethylene has not been described. The incorporation of ACC synthase antisense DNA into a geranium plant has remained elusive because the complete ACC gene sequences were not available prior to the present invention. The discoveries disclosed herein enable the production of an appropriately altered geranium plant expressing ACC synthase antisense sequences and stably producing reduced levels of ethylene.

SUMMARY OF THE INVENTION

This invention is based on the discovery and cloning of three 1-amino cyclopropane-1-carboxylate (ACC) synthase cDNA molecules representing three ACC synthase genes from *Pelargonium hortorum* cv Sincerity (red flowered cultivar of the geranium). The nucleotide sequence and corresponding amino acid sequence for each of these genes is disclosed herein. Importantly, this is believed the first report of the full-length sequence for each gene, evidenced by the ability of the cDNAs to be expressed in an expression system. Moreover, clone pPHSacc44 is shown to contain unique and important regulatory sequences.

The invention provides a method for genetic modification of geranium plants to control their levels of ethylene. The newly discovered DNA sequences, fragments thereof, or combinations of such sequences or fragments, are introduced into a plant cell in reverse orientation to inhibit expression of ACC synthase, thereby reducing the levels of endogenous ethylene.

Using the above methods, transgenic plants are to be developed and monitored for growth and development. Those plants exhibiting prolonged shelf-life with respect to plant growth, flowering, and/or reduced yellowing of leaves due to reduction in levels of ethylene are to be selected and propagated as premier products with improved properties including reduced leaf yellowing and petal abscission during shipping and storage.

The present invention is directed to an isolated DNA molecule encoding an ACC synthase enzyme of geranium which DNA molecule hybridizes with pPHSacc41 (SEQ ID NO:1), pPHSacc44 (SEQ ID NO:2), or pPHSacc49 (SEQ ID NO:3), or a functional derivative of the DNA molecule which hybridizes with SEQ ID NO:1, SEQ ID NO:2 or SEQ ID NO:3.

The isolated DNA molecule is preferably one with substantial sequence homology with a molecule selected from the group consisting of SEQ ID NO:1, SEQ ID NO:2 and SEQ ID NO:3. In one embodiment, the isolated DNA molecule is selected from the group consisting of SEQ ID NO:1, SEQ ID NO:2 and SEQ ID NO:3.

In another embodiment, the present invention provides an isolated protein encoded by a DNA molecule as described above, or a functional derivative thereof. A preferred protein has an amino acid sequence selected from the group consisting of SEQ ID NO:4, SEQ ID NO:5 and SEQ ID NO:6, or is a functional derivative thereof.

Also provided herein is an antisense oligonucleotide or polynucleotide encoding an RNA molecule which is complementary to at least a portion of an RNA transcript of the DNA molecule described above, which RNA molecule hybridizes with the RNA transcript such that expression of the ACC synthase enzyme is altered.

The above antisense oligonucleotide or polynucleotide molecule can be full length or preferably has between six and 100 nucleotides.

The antisense oligonucleotide or polynucleotide may be complementary to at least a portion of one strand of the nucleotide sequence SEQ ID NO:1, SEQ ID NO:2 or SEQ ID NO:3, or is complementary to at least a portion of an RNA sequence encoded by SEQ ID NO:1, SEQ ID NO:2 or SEQ ID NO:3. In one embodiment, the antisense oligonucleotide is complementary to at least a part of a 5' non-coding portion of one strand of the nucleotide sequence SEQ ID NO:1, SEQ ID NO:2 or SEQ ID NO:3.

An antisense oligonucleotide as described above may be complementary to at least a part of the nucleotide sequence SEQ ID NO:1 or SEQ ID NO:2 or SEQ ID NO:3, which part is, for example, from nucleotides 1–50; nucleotides 51–100; nucleotides 101–150; nucleotides 151–200; nucleotides 201–250; nucleotides 251–300 ; 301–350; 351–400; 401–450; or 451–500; or any other such contiguous group up to nucleotide 500 or even 1000.

This invention is further directed to a vector useful for transformation of a geranium plant cell, comprising:
(a) an antisense oligonucleotide or polynucleotide as described above;
(b) regulatory sequences required for expression of the oligonucleotide or polynucleotide in the cell.

The regulatory sequences comprise a promoter active in the cell, which may be an inducible promoter or preferably, a constitutive promoter. The vector preferably further comprise a polyadenylation signal.

In the above vector the promoter is preferably a heterologous promoter such as a viral promoter. A preferred viral promoter is the CaMV 35S promoter or a promoter homologous to CaMV35S.

In other embodiments, the promoter is selected from the group consisting of the SSU gene promoter, ribulose bisphosphate carboxylase promoter, chlorophyll a/b binding protein promoter, potato ST-LS 1 gene promoter, soybean heat shock protein hsp17.5-E promoter, soybean heat shock protein hsp17.3-B promoter, phenylalanine ammonia-lyase promoter, petunia 5-enolpyruvylshikimate-3-phosphate synthase gene promoter, *Rhizobium meliloti* FIXD gene promoter and nopaline synthase promoter.

Also provided is a geranium cell transformed with a vector as described above, a plantlet or mature geranium plant generated from such a cell, or a plant part from such a plant.

The present invention is further directed to a method to alter expression of an ACC synthase enzyme in a geranium cell, plant or a cutting thereof, comprising
(a) transforming a geranium cell or plant with a vector according to any of the prior directions; and
(b) allowing the antisense oligonucleotide or polynucleotide to be expressed and to hybridize with nucleic acid molecules in the cell, plant or cutting which encode the ACC synthase enzyme.

Also provided is a method of producing a geranium plant having reduced ethylene production compared to an unmodified geranium plant, comprising the steps of:
(a) transforming a geranium plant with a vector as above;
(b) allowing the plant to grow to at least a plantlet stage;
(c) testing the plant for ACC synthase enzymatic activity or ethylene production; and
(d) selecting a plant having altered ACC synthase activity and/or altered ethylene production compared to an unmodified geranium plant A geranium plant produced as above, or progeny, hybrids, clones or plants parts thereof, preferably exhibits reduced ACC synthase expression and reduced ethylene production.

In another embodiment, the invention is directed to a method for producing a geranium variety (or line), characterized by reduced expression or activity of an ACC synthase enzyme and reduced ethylene production compared to an unmodified geranium variety, comprising producing a geranium plant as above and selfing the plant to generate the variety.

Also provided is a method for producing a variant plant of a non-geranium species, an ACC synthase genes of which is homologous to a geranium ACC synthase gene, in which variant plant the ACC synthase expression is altered in comparison to an unmodified plant of the species, comprising
(a) identifying and isolating an ACC synthase gene of the species by hybridization with a sense DNA molecule as described above
(b) constructing a vector which comprises an antisense DNA sequence encoding at least a part of the gene identified in step (a) in an antisense orientation such that
(i) an RNA transcript of the antisense DNA sequence is complementary to the part of the gene, and
(ii) expression of the antisense DNA sequence alters expression of the ACC synthase gene;
(c) transforming a cell of a plant of the species with the vector of step (b) to generate a transformed cell; and
(d) regenerating a plant from the transformed cell of step (c), to produce the variant plant.

The above method is also used to produce a plant variety in a non-geranium plant species characterized by reduced expression or activity of an ACC synthase enzyme and reduced ethylene production compared to a conventional variety of the species, comprising producing a variant plant as above, and selfing the plant to generate the variety.

This invention also provides a method for genetically altering a plant, preferably a plant of a low RNA species, comprising the steps of:
(a) isolating mRNA of the plant using the 2-butoxyethanol precipitation technique wherein at least about 3–5 grams of plant tissue starting material is used to attain a critical mass amount of RNA for precipitation;
(b) constructing a cDNA library from the isolated mRNA
(c) identifying and cloning a desired DNA sequence from the library
(d) genetically altering the cloned DNA sequence;
(e) transforming cells of the plant or the plant directly with the altered DNA sequence; and
(f) if done through a cell-based technique, reproducing a plant from the cells which plant expresses the altered DNA sequence,
thereby genetically altering the plant.

In the above, method the plant is preferably a species of the genus Pelargonium or Rosa, most preferably a geranium plant. In the above method, the cloned DNA sequence preferably encodes ACC synthase. The cDNA in the above method is preferably selected from the group consisting of SEQ ID NO:1, SEQ ID NO:2 and SEQ ID NO:3.

The above method is used to produce a genetically altered geranium plant, comprising the steps of:
(a) isolating geranium mRNA using a 2-butoxyethanol precipitation technique wherein at least about 3–5 grams of plant tissue starting material is used to attain a critical mass amount of RNA for precipitation;
(b) constructing a cDNA library from the isolated mRNA
(c) identifying and cloning at least one DNA sequence from the library (d) genetically altering the cloned DNA sequence;

(e) transforming geranium cells with the altered DNA sequence; and (f) regenerating the genetically altered geranium plant from the cells, which plant expresses the altered DNA sequence.

The invention is further directed to a method of isolating plant mRNA, comprising the steps of:

(a) extracting nucleic acids from a sufficient amount of plant tissue starting material to attain a critical mass amount of RNA for precipitation;

(b) isolating RNA from the nucleic acids of step (a) using a 2-butoxyethanol precipitation technique;

(c) contacting the RNA with a binding partner for mRNA, for example oligo-dT or another molecule or entity which has the characteristics of binding specifically to mRNA with the exclusion of other forms of RNA or DNA. The binding partner may be immobilized on a solid phase or carrier; this yields immobilized mRNA; and (d) eluting the immobilized mRNA from the carrier by conventional elution methods, or obtaining bound mRNA, thereby isolating the mRNA from total RNA.

BRIEF DESCRIPTION OF THE DRAWINGS

FIG. 3 shows the nucleotide sequence of the cDNA clone designated pPHSacc41 (SEQ ID NO:1). The following landmarks are indicated: the short 5' sequence originating in the vector are in italics and underscored; the start ATG codon is in bold and underscored; the termination codon of the coding sequence (TAA or TAG) is in bold and double underscored; the polyadenylation signal (sequence) near the 3' end is shown in bold (AATAAA or AAATAA).

FIGS. 4 and 4a show the nucleotide sequence of the cDNA clone designated pPHSacc44 (SEQ ID NO:2). Landmarks are as shown in FIG. 3.

FIG. 5 shows the nucleotide sequence of the cDNA clone designated pPHSacc49 (SEQ ID NO:3). Landmarks are as shown in FIG. 3.

FIG. 6 shows the deduced amino acid sequence (SEQ ID NO:4) encoded by nucleotide sequence SEQ ID NO:1.

FIG. 7 shows the deduced amino acid sequence (SEQ ID NO:5) encoded by nucleotide sequence SEQ ID NO:2.

FIG. 8 shows the deduced amino acid sequence (SEQ ID NO:6) encoded by nucleotide sequence SEQ ID NO:3.

DESCRIPTION OF THE PREFERRED EMBODIMENTS

Figure 1:
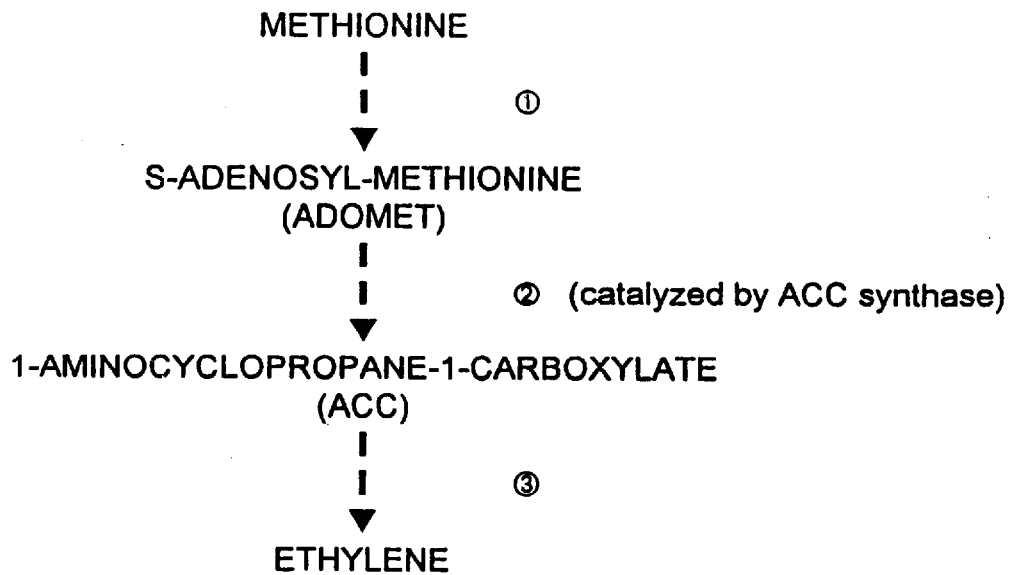
FIG. 1 shows the ethylene biosynthetic pathway including the step catalyzed by ACC synthase.

The present inventor has isolated, cloned and identified several cDNA sequences encoding the enzyme ACC synthase in geranium plants (specifically from *Pelargonium hortorum* cv Sincerity). These cDNA sequences correspond to genes which are important in the control of ethylene production. The DNA is expressed in any of a number of expression systems, including an in vitro expression system to yield a polypeptide product which preferably has ACC synthase enzymatic activity.

Cloned ACC synthase gene(s) or fragments thereof, when introduced in reverse orientation (antisense) under control of a strong promoter (discussed below in detail), such as the cauliflower mosaic virus promoter CaMV35S, can be used to genetically modify a geranium plant. Selected antisense sequences sharing sufficient homology to ACC synthase genes in other plants can be used to achieve similar genetic modification. One result of this modification is a reduction in the amount of translatable ACC synthase-encoding mRNA. As a consequence, the amount of ACC synthase produced in the plant cells is reduced, thereby reducing the rate of conversion of ACC to ethylene. This genetic modification can effect a permanent change in ethylene levels in the modified plant and be propagated in offspring plants by selfing or other reproductive schemes. Hence, the invention provides a plant modified as described herein as well as plants which although modified in a different manner achieve similar results or utilize similar concepts as disclosed herein. The genetically altered plant is used to produce a new variety or line of plants wherein the alteration is stably transmitted from generation to generation.

The geranium plant is one of the most ethylene-sensitive flowering plants (Nell, T. A., 1993, In: White, J. W., ed., *Geranium IV. The Growers Manual*, Edition Four, Ball Publishing, Geneva, Ill., pp 171–172). A change in ethylene levels may thus have a great impact on its commercial desirability. The present invention provides isolated ACC synthase genes obtained specifically from geranium for use in genetic modification preferably of geranium plants. The full length DNA molecules described herein are unique to geraniums and vary significantly in sequence from ACC synthase DNA in any other unrelated plant species.

Because of such interspecies variation, to achieve stable genetic modification, it may be important that an ACC synthase gene or gene fragment (a) be obtained from the same species or (b) be a functional derivative of the DNA sequence native to the species. However, it is possible that a selected sequence from one plant genus or species may be employed using antisense technology in a different genus or species to achieve a useful effect such as that described here. The present invention thus provides for the first time the appropriate DNA sequences which may be used to achieve a stable genetic modification primarily of geranium plants (and of other plants as well).

For the identification, in general, preparation of plasmid DNA, restriction enzyme digestion, agarose gel electrophoresis of DNA, Southern blots, Northern blots after separation of the RNA on a formaldehyde agarose gel, DNA ligation and bacterial transformation were carried out using conventional methods well-known in the art. See, for example, Sambrook, J. et al., *Molecular Cloning: A Laboratory Manual*, 2nd Edition, Cold Spring Harbor Press, Cold Spring Harbor, N.Y., 1989.

As used herein, the term "plant" refers to either a whole plant, a plant part, a plant cell, or a group of plant cells. The types of plants which can be used in the method of the invention generally includes the genus Pelargonium (geraniums) which can take up and express the DNA molecules of the present invention. It may include plants of a variety of ploidy levels, including haploid, diploid, tetraploid, and polyploid.

A "transgenic plant" is defined as a plant which is genetically modified in some way, including but not limited to a plant which has incorporated heterologous DNA or modified DNA or some portion of heterologous or homologous DNA into its genome. The altered genetic material may encode a protein, comprise a regulatory or control sequence, or may comprise an antisense sequence or encode an antisense RNA which is antisense to an endogenous DNA or mRNA sequence of the plant. A "transgene" or a "transgenic sequence" is defined as a foreign or atypical gene or partial sequence which has been incorporated into a transgenic plant.

As used in the present application, the term "substantial sequence homology" or "substantially homologous" is used to indicate that a nucleotide sequence (in the case of DNA or RNA) or an amino acid sequence (in the case of a protein or polypeptide) exhibits substantial functional or structural equivalence with another nucleotide or amino acid sequence. Any functional or structural differences between sequences having substantial sequence homology will be de minimis; that is, they will not affect the ability of the sequence to function as indicated in the desired application. Differences may also be simply due to inherent variations in codon usage among different species. Sequences that have substantial sequence homology with the sequences disclosed herein are usually "variants" of the disclosed sequence, such as mutations, but may also be synthetic sequences. Structural differences are considered de minimis if there is a significant amount of sequence overlap or similarity between two or more different sequences or if the different sequences exhibit similar physical characteristics even if the sequences differ in length or structure. Such characteristics include, for example, ability to hybridize under defined conditions, or, in the case of proteins, immunological crossreactivity, similar enzymatic activity, etc.

Additionally, two nucleotide sequences are substantially homologous if the sequences have at least 70 percent, more preferably 80 percent and most preferably 90 percent sequence similarity between them. Two amino acid sequences are substantially homologous if they have at least 50 percent, preferably 70 percent, and most preferably 90 percent similarity between the active portions of the polypeptides.

The term "hybridization" as used herein is generally understood to mean hybridization at appropriate conditions of stringency as would be readily evident to those skilled in the art depending upon the nature of the probe sequence and target sequences. Conditions of hybridization and washing are well-known in the art, and the adjustment of conditions depending upon the desired stringency by varying incubation time and temperature and ionic strength of the solution are readily accomplished. See, for example, Sambrook, J., et al., *Molecular Cloning: A Laboratory Manual*, Second Edition, Cold Spring Harbor Press, Cold Spring Harbor, N.Y. (1989). The choice of conditions is dictated by the length of the sequences being hybridized, in particular the length of the probe sequence, the relative G-C content of the nucleic acid and the amount of mismatches to be permitted. Low stringency conditions are preferred when partial hybridization between strands that have lesser degrees of complementarity is desired. When perfect or near-perfect complementarity is desired, high stringency conditions are preferred. For typical high stringency conditions, the hybridization solution contains 6×SSC, 0.01M EDTA, 5×Denhardt's solution and 0.5% SDS. Hybridization is carried out at about 68° C. for 3–4 hours for fragments of cloned DNA and 12–16 hours for total eukaryotic DNA. For lower stringency, the temperature is reduced to about 12° C. below the melting temperature ($T_m$) of the duplex. The $T_m$ is known to be a function of G-C content and duplex length as well as the ionic strength of the solution.

By "functional derivative" of a nucleic acid (or poly- or oligonucleotide) is meant a "fragment," "variant," "homologue" or "analogue" of the gene or DNA sequence encoding ACC synthase, or in some way related to the production or use of ACC synthase, especially geranium ACC synthase. A functional derivative may retain at least a portion of the function of the ACC synthase-encoding DNA which permits its utility in accordance with one embodiment of the present invention. Such function may include the ability to hybridize with native geranium or homologous DNA from another plant which encodes ACC synthase or with an mRNA transcript thereof, or, in antisense orientation, to inhibit the transcription and/or translation of geranium ACC synthase mRNA, or the like.

A "fragment" of the gene or DNA sequence refers to any subset of the molecule, that is, a shorter polynucleotide- or oligonucleotide. A "variant" refers to a molecule substantially similar to either the entire gene or a fragment thereof, such as a nucleotide substitution variant having one or more substituted nucleotides but which maintains the ability to hybridize with the particular gene or to encode a mRNA transcript which hybridizes with the native DNA. A "homologue" refers to a fragment or variant sequence from a different plant genus or species. An "analogue" refers to a non-natural molecule substantially similar to or functioning in relation to either the entire molecule, the variant, or to a fragment thereof.

"Altered" expression" or an "alteration" of expression of a gene (most particularly of ACC synthase), as used herein, refers to any process or result whereby the normal expression of the gene, for example that occurring in an "unmodified" geranium plant, defined as a known, conventional, naturally-occurring geranium plant, is changed in some fashion. As intended herein, an alteration is a complete or preferably a partial reduction in the expression of ACC synthase, but may also include a change in the timing of expression, or another state wherein the expression of ACC synthase differs from that which would be most likely to occur naturally in an unmodified geranium plant, variety or cultivar. A preferred alteration is one which results in a decrease in ethylene production by the plant compared to ethylene production in an unmodified plant.

In producing a genetically altered plant according to this invention, it is preferred to select individual plantlets or plants by the desired trait, generally reduced ACC synthesis expression and reduced ethylene production. Expression of ACC synthase can be measured by quantitating the amount of ACC synthase mRNA using conventional hybridization techniques. Alternatively, the amount of ACC synthase protein can be quantitated, for example in a conventional immunoassay method using a specific antibody such as those described herein. Finally, the ACC synthase enzymatic activity can be measured using biochemical methods as described in Kionka et al., supra; Amrhein et al., supra; or Hoffman N. E., et al., supra. Ethylene biosynthesis in the plantlet or plant can be quantitated using known methods Yang, S. F. et al. (1984), *Annu. Rev Plant Physiol:* 35, 155–189); Abeles, F. B. et al. eds, *Ethylene in Plant Biology*, Academic Press, New York, 1976 White, J. W., ed., *Geranium IV. The Growers Manual*, Edition Four, Ball Publishing, Geneva, Ill.

In order for a newly inserted gene or DNA sequence to be expressed, resulting in production of the protein which it encodes (or, in the case of antisense DNA, to be transcribed, resulting in an antisense RNA molecule), the proper regulatory signals should be present in the proper location with respect to the coding or antisense sequence. These regulatory signals may include a promoter region, a 5' non-translated leader sequence and a 3' polyadenylation sequence as well as enhancers and other known regulatory sequence. The promoter is a DNA sequence that directs the cellular machinery to transcribe the DNA to produce RNA. The promoter region influences the rate at which the mRNA product and, if the DNA encodes a protein, the resultant protein product, are made. The 3'-polyadenylation signal is a non-translated region that functions in plant cells to cause the addition of a polyadenylate stretch to the 3' end of the mRNA to stabilize it in the cytoplasm for subsequent translation.

A promoter DNA sequence is operably linked to a second DNA sequence and regulates its transcription. If the second DNA sequence encodes a protein, the promoter DNA sequence is said to be "operably linked" if it affects the transcription of the mRNA encoding the protein product from the second DNA sequence. A DNA sequence comprising a promoter is generally physically near the coding sequence in the same recombinant construct, though physical contiguity is not required. "Strong" promoters are able to direct RNA synthesis at higher rates than weaker promoters. Certain promoters direct RNA production at higher levels only in particular types of cells and tissues. Promoters that direct RNA production in many or all tissues of a plant without the need for "induction" by a specific inducer substance are called constitutive promoters. The operation of a constitutive promoter is relatively independent of the developmental stage of the cell in which it is contained and is most preferred for the present invention. An inducible promoter is one which, in response to the presence of an inducer, is activated. Hence, a coding sequence driven by an inducible promoter can be turned on or off by providing or withdrawing the inducer. A promoter may be homologous, derived from the same species as the coding sequence. Preferably, the promoter is heterologous, that is, derived from another species, or even from a virus.

Expression levels from a promoter which is useful for the present invention can be tested using conventional expression systems, for example, by measuring levels of a reporter gene product (protein or mRNA) in extracts of the leaves, stems, roots and flowers of a transgenic plant into which the promoter/reporter have been introduced.

Cauliflower mosaic virus (CaMV) is a double-stranded DNA plant virus. It contains two promoters responsible for the production of transcripts of 35S and 19S in size in infected plants (Guilley, H., et al., *Cell* 30: 763 (1982)). The 35S promoter (CaMV35S) is one of the strongest constitutive heterologous promoters known in plants (Odell, et al., *Nature* 313: 810–812 (1985); Jensen, et al., *Nature* 321: 669–674 (1986); Jefferson, et al., *EMBO J.* 6: 3901–3907 (1987); Kay, et al., *Science* 236: 1299–1302 (1987); Sanders, et al., *Nucl. Acids Res.* 4: 1543–1558 (1987)). Two different domains within the CaMV 35S promoter may differentially regulate expression of a coding sequence in different plant tissues (domain A, from nucleotides −90 to +8) vs. domain B from nucleotides −343 to −90), as described by Benfey, et al., 1989 *EMBO J.* 8: 2195–2202). The CaMV35S promoter is active in isolated protoplasts (Fromm, M., et al., *Proc. Natl. Acad. Sci. USA* 82: 5824 (1985)) and is expressed in all organs of various transgenic plants in the absence of any viral protein, making it widely used in plant genetic engineering.

Because of variability in the expression of genes driven by the CaMV35S promoter, (which may be either an intrinsic property of the promoter or a result of variability in the position at which CaMV35S promoter-driven DNA sequence is integrated into the genome of the transformed plant), CaMV35S may be particularly useful for effecting different degrees altered gene expression by an antisense sequence which the promoter controls. Additional useful plant promoters in, for example, other caulimoviruses (a group of double-stranded DNA viruses to which the cauliflower mosaic virus belongs) have also been developed and are useful for similar applications. Two caulimoviruses distantly related to CaMV are the figwort mosaic virus (FMV) (Richins, et al., *Nucl. Acids Res.* 15: 8451–8466 (1987)) and the carnation etched ring virus (CERV) (Hull, et al., *EMBO J.* 5: 3083–3090 (1986). The promoters of FMV and CERV which are homologues of the CaMV35S promoter are described in Rogers, U.S. Pat. No. 5,378,619. Any of the foregoing viral promoters, as well as other viral promoters which act as strong promoters for expression of plant DNA sequences in plant cells, may be used to drive the expression of the DNA molecules of the present invention.

Certain other strong plant promoters are also useful to direct the expression of the ACC synthase DNA (or antisense sequences) of the present invention. For example, the small subunit (SSU) of the enzyme ribulose-1,5-bisphosphate carboxylase (RuBPCase), the primary enzyme of the carbon fixation pathway in chloroplasts of plants of the C3 class is an example of a polypeptides known to be highly expressed in plants. A highly efficient SSU promoter DNA such as the promoter DNA from the SSU gene denominated SSU301 from Petunia (Bedbrook, et al., U.S. Pat. No. 4,962,028) may be used herein. The promoter may be used in the form of an isolated 5' fragment of the SSU gene, and preferably has the 3' end of the fragment modified to create a restriction site which permits ready fusions with the ACC synthase antisense DNA of the present invention. The promoter may be conveniently arranged to form an expression cassette comprising a 5' fragment (the promoter region of the SSU gene), a 3' fragment and a linker region connecting the two fragments. The fusion points between the 5' fragment and the linker region and between the 3' fragment and the linker region are preferably modified to create restriction sites which permit the antisense DNA of the present invention to be substituted for the linker so as to yield "chimeric" genes containing the complete proximal 5' and 3' regions of the SSU gene but none of the SSU coding sequence.

Other plant promoter enhancer/sequences which may be used in accordance with the present invention have been described in the following references: Coruzzi, et al., 1984, *EMBO J.* 3: 1671–1680; Herrera-Estrella, et al., 1984, *Nature* 310: 115–120; Apel, et al., 1978, *Eur. J. Became.* 85: 581–588; Stiekema, et al., 1983, *Plant Physiol.* 72: 717–724; Thompson, et al., 1983, *Planta* 158: 487–500; Jones, et al., 1985, *EMBO J.* 4: 2411–2418; Stockhaus, et al., 1989, Plant Cell 1: 805–814; Gurley, et al., 1986, *Mol. Cell Biol.* 6: 559–565; Landsmann, et al., 1988, *Mol. Gen. Genet.* 214: 68–73; Bevan, et al., 1989, *EMBO J.* 8: 1899–1906; Benfey, et al., 1989, *Science* 244: 174–181.

Certain bacterial promoters have been observed to be expressed in plants, including the *Rhizobium meliloti* FIXD gene promoter (Puhler, et al., U.S. Pat. No. 4,782,022) and the nopaline synthase promoter (Ha, et al., 1989, *Nucl. Acids Res.* 17: 215–224; An et al., 1988, *Plant Physiol.* 88: 547–552). Several promoter sequences, termed the rol A, B and C promoters, have been identified in *Agrobacterium rhizogenes* (Schmulling, et al., 1989, *Plant Cell* 1: 665–670; Sugaya, et al., 1989, *Plant Cell Physiol.* 30: 649–654).

To test the activity of a promoter, *E. coli* β-glucuronidase (GUS) coding sequence or a mutant Arabidopsis EPSP synthase gene which encodes an enzyme tolerant of glyphosate herbicides may be used as a reporter gene. Transformed plant cells or plants containing the GUS gene operably linked to the promoter being tested are assayed using a histological staining procedure to determine GUS activity in the transformed cells.

The present invention provides antisense oligonucleotides and polynucleotides complementary to the gene or genes encoding ACC synthase in geranium plants. Such antisense oligonucleotides, should be at least about six nucleotides in length to provide minimal specificity of hybridization, and may be complementary to one strand of DNA or to mRNA encoding ACC synthase (or to a portion thereof), or to flanking sequences in genomic DNA which are involved in regulating ACC synthase gene expression. The antisense oligonucleotide may be as large as about 100 nucleotides, an may extend in length up to and beyond the full coding sequence for which it is antisense. The oligonucleotides can be DNA or RNA or chimeric mixtures or derivatives or modified versions thereof, single-stranded or double-stranded.

The action of the antisense nucleotide may result in specific alteration, primarily inhibition, of ACC synthase gene expression in cells. For a general discussion of antisense, see: Alberts, B., et al., *MOLECULAR BIOLOGY OF THE CELL*, 2nd Ed., Garland Publishing, Inc., New York, N.Y. (1989), in particular, pages 195–196, which reference is hereby incorporated by reference).

The antisense oligonucleotide may be complementary to any portion of the ACC synthase encoding sequence. In one embodiment, the antisense oligonucleotide may be between about 6 and 100 nucleotides, and may be complementary to the initiation ATG codon and an upstream, non-coding translation initiation site of the ACC synthase sequence. For example, antisense nucleotides complementary primarily for non-coding sequence, are known to be effective inhibitors of the expression of genes encoding transcription factors (Branch, M. A., 1993 *Molec. Cell. Biol.* 13: 4284–4290).

Preferred antisense oligonucleotides are complementary to a portion of the mRNA encoding ACC synthase. For instance, it is expected that by introducing a full length cDNA clone gene in an antisense orientation, successful alteration of gene expression will be most probable. Naturally, introduction of partial sequences, targeting to specific regions of the gene, and the like can be effective as well. An example of a preferred antisense oligonucleotide is a 50 mer which is antisense to 50 nucleotides in the 5'half of an RNA transcript of an ACC-encoding cDNA (such as SEQ ID NO:1, SEQ ID NO:2 or SEQ ID NO:3), more preferably any stretch of 50 nucleotides in the first 500 nucleotides of the 5' part of the RNA transcript. For example, the antisense oligonucleotide can be antisense to nucleotides 1–50, 2–51, 3–52, 4–53,5–54, etc., of the RNA transcript. Alternatively, the antisense oligonucleotide can be shorter, for example a 30-mer, and be antisense to any 30 nucleotide stretch of the RNA transcript, preferably in the first 500 5' nucleotides.

As is readily discernible by one of ordinary skill in the art, the minimal amount of homology required by the present invention is that sufficient to result in sufficient complementarity to provide recognition of the specific target RNA and inhibition or reduction of its translation or function while not affecting function of other mRNA molecules and the expression of other genes. While the antisense oligonucleotides of the invention comprises sequences complementary to at least a portion of an RNA transcript of ACC synthase, absolute complementarity, although preferred, may not be required. A sequence "complementary to at least a portion of" another sequence, as referred to herein, may have sufficient complementarity to be able to hybridize with that other sequences in vivo, perhaps forming a stable duplex.

Naturally, the ability to hybridize may depend on both the degree of complementarity and the length of the antisense nucleic acid. Generally, the longer the hybridizing nucleic acid, the more base mismatches with the ACC synthase target sequence it may contain and still form a stable duplex. One skilled in the art can ascertain a tolerable degree of mismatch by use of standard procedures to determine the melting temperature of the hybridized complex as discussed above and other techniques.

The antisense RNA oligonucleotides may be generated intracellularly by transcription from exogenously introduced nucleic acid sequences. Thus, antisense RNA may be delivered to a cell by transformation or transfection or infection with a vector, such as a plasmid or a virus, into which is incorporated (a) DNA encoding the antisense RNA and operably linked thereto (b) the appropriate regulatory sequences, including a promoter, to express the antisense RNA in a target host cell (and whole plant). Within the cell the exogenous DNA or a portion thereof may be transcribed, producing an antisense RNA of the invention. Vectors can be plasmid, viral, or others known in the art which are used for replication and expression in plant cells. Expression of the sequence encoding the antisense RNA can be by any promoter known in the art to act in plant, preferably geranium, cells. Such promoters can be inducible or preferably are constitutive as described above. Such a vector, preferably a plasmid, becomes chromosomally integrated such that it can be transcribed to produce the desired antisense RNA. Such plasmid or viral vectors can be constructed by recombinant DNA technology methods that are standard in the art.

An oligonucleotide, between about 6 and about 100 bases in length and complementary to the target sequence of ACC synthase, as describe above may be prepared by chemical synthesis from mononucleotides or shorter oligonucleotides, or produced by recombinant means.

Basic procedures for constructing recombinant DNA and RNA molecules in accordance with the present invention are disclosed by Sambrook, J., et al., In: *Molecular Cloning: A Laboratory Manual*, Second Edition, Cold Spring Harbor Press, Cold Spring Harbor, N.Y. (1989), which reference is herein incorporated by reference. Oligonucleotide molecules having a strand which encodes antisense RNA complementary to an ACC synthase sequence can be prepared using procedures which are well known to those of ordinary skill in the art. Details regarding such procedures are described in: Belagaje, R., et al., *J. Biol. Chem.* 254: 5765–5780 (1979); Maniatis, T., et al., In: *MOLECULAR MECHANISMS IN THE CONTROL OF GENE EXPRESSION*, Nierlich, D. P., et al., eds., Acad. Press, N.Y. (1976); Wu, R., et al., *Prog. Nucl. Acid Res. Molec. Biol.* 21: 101–141 (1978); Khorana, H. G., *Science* 203: 614–625 (1979)). Automated synthesizers may be used for DNA synthesis (such as are commercially available from Biosearch, Applied Biosystems, etc.).

Techniques of nucleic acid hybridization are disclosed by Sambrook et al. (supra), and by Haymes, B. D., et al., In: *NUCLEIC ACID HYBRIDIZATION, A PRACTICAL APPROACH*, IRL Press, Washington, D.C. (1985)), which references are herein incorporated by reference.

The transgenic plants of the present invention may be prepared by DNA transformation using any method of transformation known in the art. These methods include transformation by direct infection or co-cultivation of plants, plant tissue or cells with *Agrobacterium tumefaciens* (Horsch, et al., *Science* 225: 1229 (1985); Marton, *Cell Culture and Somatic Cell Genetic of Plants* 1: 514–521

(1984)); Fry, et al., *Plant Cell Reports* 6: 321–325 (1987); direct gene transfer into protoplasts or protoplast uptake (Paszkowski, et al., *EMBO J.* 12: 2717 (1984); Loerz, et al., *Mol. & Gen. Genet.* 178: 1199 (1985); electroporation Fromm, et al., *Nature* 319: 719 (1986)); microprojectile or particle bombardment (Klein, et al., *Bio/Technology* 6: 559–563 (1988)); injection into protoplasts cultured cells and tissues (Reich et al., *Bio/Technology*, 4: 1001–1004 (1986)); or injection into meristematic tissues of seedlings and plants (De La Pena, et al., *Nature,* 325: 274–276 (1987); Graves, et al., *Plant Mol. Biol.* 7: 43–50 (1986); Hooykaas-Van Slogteren, et al., *Nature* 311: 763–764 (1984); Grimsley, et al., *Bio/Technology* 6: 185 (1988); and Grimsley, et al., *Nature* 325: 177 (1988);

The *Agrobacterium tumefaciens* strain 208 carrying the disarmed pMP90RK plasmid can be used to achieve transformation. Used for plant transformations, the vector plasmid may be introduced into the Agrobacterium by the triparental conjugation system (Ditta, et al., (1980) *Proc. Natl. Acad. Sci.* USA 77: 7347–7451) using the helper plasmid pRK2013. The vectors may be transferred to plant cells by the vir functions encoded by the disarmed pMP90RK Ti plasmid. The vector is opened at the pTiT37 right border sequence and the entire vector sequence is inserted into the host plant chromosome. The pMP9ORK Ti plasmid is probably not transferred to the plant cell but remains in the Agrobacterium.

Normally, regeneration will be involved in obtaining a whole plant from the transformation process. The term "regeneration" as used herein, means growing a whole plant from a plant cell, a group of plant cells, a plant part or a plant piece (e.g. from a protoplast, callus, tissue part, or explant, etc.) Plant regeneration from cultured protoplasts is described in Evans, et al., *Handbook of Plant Cell Cultures* 1: 124–176 (MacMillan Publishing Co. New York 1983); Davey, M. R., *Protoplasts* (1983), Lecture Proceedings, pp. 12–29, Birkhauser, Basel, 1983); P. J. Dale, ibid, at pp. 31–41, (Birkhauser, Basel 1983); and H. Binding, *Plant Protoplasts*, pp. 21–73, CRC Press, Boca Raton, 1985).

Plant parts obtained from the regenerated plant in which expression of an ACC synthase gene has been altered, such as flowers, seeds, leaves, branches, fruit, and the like are included within the definition of "plant" as stated above, and are included within the scope of the invention. Progeny and variants and mutants of the regenerated plants are also included, especially if these parts comprise the introduced DNA sequences.

The present invention also provides ACC synthase proteins encoded for by the cDNA molecules described above. Such proteins preferably have the amino acid sequences SEQ ID NO:4, SEQ ID NO:5 or SEQ ID NO:6 shown in FIGS. 6, 7, and 8. These proteins, or functional derivatives thereof, are preferably produced by recombinant methods optionally in combination with chemical methods.

A "functional derivative" of the ACC synthase protein is a "fragment," "variant," "analog," or "chemical derivative" of ACC synthase, which retains at least a portion of the function of the ACC synthase which permits its utility in accordance with the present invention. Such function includes enzymatic activity or immunological crossreactivity with an antibody specific for ACC synthase. A fragment of the ACC synthase protein refers to any subset of the molecule, that is, a shorter peptide. A variant refers to a molecule substantially similar to either the entire protein or a fragment thereof. Variant peptides may be conveniently prepared by direct chemical synthesis using methods well-known in the art. An "analog" of ACC synthase refers to a non-natural protein substantially similar to either the entire protein or a fragment thereof. A chemical derivative of ACC synthase contains additional chemical moieties not normally a part of the protein or peptide fragment thereof Covalent modifications of an ACC synthase peptide are included within the scope of this invention. Such modifications may be introduced into the molecule by reacting targeted amino acid residues of the peptide with an organic derivatizing agent that is capable of reacting with selected side chains or terminal residues.

A protein or peptide according to the present invention may be produced by culturing a cell transformed with a DNA sequence of this invention, allowing the cell to synthesize the protein, and obtaining the protein from the culture medium if it is secreted, or if it is intracellular, obtaining it by extraction. In a preferred embodiment, the protein is produced in a cell free system, for example, as described by Ranu, R. S., et al, 1979, *Meth. Enzymol.* 60: 459–484 and Ranu, R. S., et al, (1996) *Gene Expression* 5: 143–153.

To produce an isolated, purified protein or peptide, the in vitro translation product or the cell or tissue extract from transformed plant cells or plant parts is subjected to conventional biochemical purification methods, including but not limited to affinity chromatography using an antibody specific for an epitope of the protein.

Having now generally described the invention, the same will be more readily understood through reference to the following examples which are provided by way of illustration, and are not intended to be limiting of the present invention, unless specified.

EXAMPLES

Plant Material

*Pelargonium hortorum* cv sincerity (geranium) plants grown and maintained in a greenhouse were used to clone the cDNA corresponding to ACC synthase genes. Flower tissue in the form of senescing flower petals (from different stages) were collected in liquid nitrogen and used immediately or stored at −70° C. until use.

Messenger RNA (mRNA) isolation

The quality of the mRNA largely determines the quality of cDNA library generated subsequently for cDNA cloning of ACC synthase gene. By "quality of the mRNA" is intended the presence of all the desired mRNA species, especially those mRNA molecules that are present in cells in relatively low abundance (either because of the number of gene copies, the rate of transcription or the stability of the mRNA). The most widely used method for preparation of RNA utilizes extraction with 4M guanidine thiocyanate of total RNA (Chomczynski, P., et al. (1987), *Anal. Biochem.* . 162: 156–159). When this method was tried by the present inventor, the quality of RNA obtained was inadequate and did not permit a generation of a useable, high quality cDNA library (containing cDNA inserts corresponding to the least abundant mRNAs). Thus, when cDNA libraries prepared using the conventional method were screened for the presence of cDNA inserts encoding ACC synthase, the clones identified contained only partial genes or, mostly frequently, false positives. This problem alone made the process of isolating the ACC synthase genes of this invention extremely difficult and challenging. This conclusion was also suggested from the results of expression screening of such libraries with antibodies specific for the ACC synthase protein. In sum, the prior art RNA isolation technique at best invited experiments to try to find the full length genes, but provided no reasonable expectation of success. Problems posed by the poor quality of the total RNA prepared using conventional methods led the present inventor to look for alternative means for obtaining RNA of sufficiently high quality to be useful for the purposes of this invention, namely preparation of a cDNA library having a high probability of including a full length DNA sequences corresponding to low-abundance mRNAs, in particular full-length ACC synthase coding sequences.

Preparation of RNA

The preferred method discovered by the present inventor was based on the precipitation of RNA from a tissue extract using 2-butoxyethanol (Manning, K., 1991, *Anal. Biochem.* 195: 45–50) with modifications. This method is referred to herein as "a 2-butoxyethanol precipitation technique." This technique was originally developed for RNA isolation, and by adapting it for mRNA isolation, the extraordinary results of this invention were achieved. Generally, in order to achieve the required RNA precipitation, a co-precipitation critical mass of RNA must be present in the preparation. The relative low proportion of RNA in relation to the total extracted material required the recognition by the present inventor that the standard amount of tissue extract used in RNA preparation, about 1 gram or less, would be insufficient for certain types of plants such as geranium (discussed more fully below). The success described herein was ultimately attained by using an unusually large amount of tissue. Foreffort with geranium, this was about 3–5 grams. While, in hindsight, this may seem like a simple problem and solution, in fact, this problem does not appear to have been considered by others, and, therefore, the novel method is not an obvious modification of the older technique.

This problem in part stems from the fact that the desired precipitation is "non-linear," meaning that no simple linear relationship exists between the mass of RNA and the amount of precipitation. Rather, the process is a threshold phenomenon, and unless that critical mass is present, precipitation will not occur. For these reasons, the prior art technique would appear on its face to be inapplicable for obtaining a high quality mRNA preparation from woody plants such as geranium. Surpassing such a critical amount of RNA, that is, an amount at which precipitation occurs, permitted the method, as modified, to demonstrate its full utility. Hence, the present inventor achieved an unexpected and extraordinary result, in spite of the fact that the technology underlying the modifications introduced to earlier methods had been available. Those of ordinary skill in the art may have appreciated (although this is not evident) that a key impediment was in the obtaining of high quality mRNA to generate a fully representative cDNA library. Furthermore, a long felt need in the art for such a library had not been satisfied. Nevertheless, substantial attempts in the prior art failed because practitioners did not understand the true nature of the reasons for failure of this type of technique.

The present inventor's discovery of a means to here achieve the co-precipitation critical mass of RNA is particularly important to the class of plants which have a low proportion of RNA in their tissue, such as less than only $\frac{1}{10,000}$th of the total tissue usually obtained. It is also particularly important for woody plants such as geranium, for which the present invention is particularly useful. These groups of plants comprises plant species that have a low proportion of RNA in their tissue relative to non-nucleic acid material. This is in contrast to other plants which have a higher proportion of RNA and are amenable to the preparation of high quality mRNA (and cDNA corresponding thereto) by the traditional approaches of the prior art. While this "low RNA" group of plants is known to include at least Pelargonium species and Rosa (rose) species, it is clear that other plants also fall in this category, as would be evident to those skilled in the art. This group of plants is characterized in one manner as being woody (that is, they contain large amounts of fiberous material) and therefore having a low relative abundance of RNA, or conversely, as a high relative proportion of non-nucleic acid material. Thus, in this category of low RNA plants, it would be necessary to use a "large" amount of tissue, namely, an amount which (depending upon the particular plant or technique) is sufficient to yield a co-precipitant critical mass of total RNA in the process. For Pelargonium, Rosa, and the like, a co-precipitant critical mass of RNA is about 200 μg for successful implementation of the 2-butoxyethanol precipitation technique described herein. (Other RNA isolation techniques or plants may, of course, each have their own critical mass, that is, the presence of enough total RNA for precipitation to actually occur.) Thus, for the present technique and plants, about 3–5 grams of flower tissue was used initially. This may represent a minimum amount for some plants. Naturally more would also work.

The flower tissue was ground into a powder using a pestle and mortar precooled by liquid nitrogen. The resulting material was then ground with 12–20 ml of extraction buffer (0.2M boric acid/Tris-HCl and 10 mM EDTA (pH 7.6)), followed by addition of 0.24–0.4 ml of 25% sodium dodecyl sulfate (SDS) and 0.24–0.4 ml of 2-mercaptoethanol (2-ME).

The mixture was brought to room temperature and extracted with an equal volume of extraction buffer, saturated phenol/chloroform mixture. The mixture was centrifuged at 20,000×g at room temperature. The upper aqueous phase was collected and kept in a fresh tube. The interphase and lower organic phase were re-extracted with an equal volume of extraction buffer containing SDS and 2-ME. After centrifugation at 20,000×g, the second aqueous phase was removed and combined with the first aqueous phase. The pooled aqueous phase was diluted with 2.5 volume of water and a quantity of 1M sodium acetate (pH 4.5) sufficient to make the final concentration 80 mM.

This was followed by addition of 0.4 volumes of 2-butoxyethanol (2-BE). After 30 minutes on ice, the mixture was centrifuged at 20,000×g for 10 minutes at 0° C. The clear supernatant was collected. Additional 2-BE was added to bring the total to one volume. After 30 minutes on ice, the nucleic acid-containing pellet was collected by centrifugation at 20,000×g for 10 minutes at 0° C. The pellet was washed first with a 1:1 (v/v) mixture of extraction buffer and 2-BE, followed by 70% ethanol containing 0.1M potassium acetate (pH 6.0), and finally with 100% ethanol. The pellet was then air dried.

The nucleic acid pellet was dissolved in water to a concentration of about 1 mg/ml and sufficient 12M LiCl was added to bring the LiCl concentration to 3M. After one hour on ice, an RNA precipitate was collected by centrifugation at 12,000×g for 10 minutes at 0° C. The pellet was washed twice with 3M LiCl and once with 70% ethanol and was finally air dried. RNA was dissolved 0.2–0.5 ml of 10 mM Tris-HCl, 1 mM EDTA (pH 8.0) (TE buffer).

Isolation of mRNA

PolyA$^+$mRNA was isolated by binding to Dynabeads-oligo(dT)25 (Dynal, Inc., Lake Success, N.Y.). The oligo (dT)25 is a preferred binding partner, in addition others are known in the art, the key function being merely the ability to selectively attach to the mRNA. For this binding partner, the protocol provided by the manufacturer was used. PolyA+ RNA was bound to Dynabeads in the presence of 1×binding buffer for 30 minutes. The Dynabeads serve as one of the many possible solid phase supports or carriers. This served to immobilize the mRNA. The beads were washed three times with washing buffer containing lithium dodecyl sulfate (LiDS) and once with wash buffer alone. mRNA was eluted from the beads with 50 μl of TE buffer.

Figure 2:
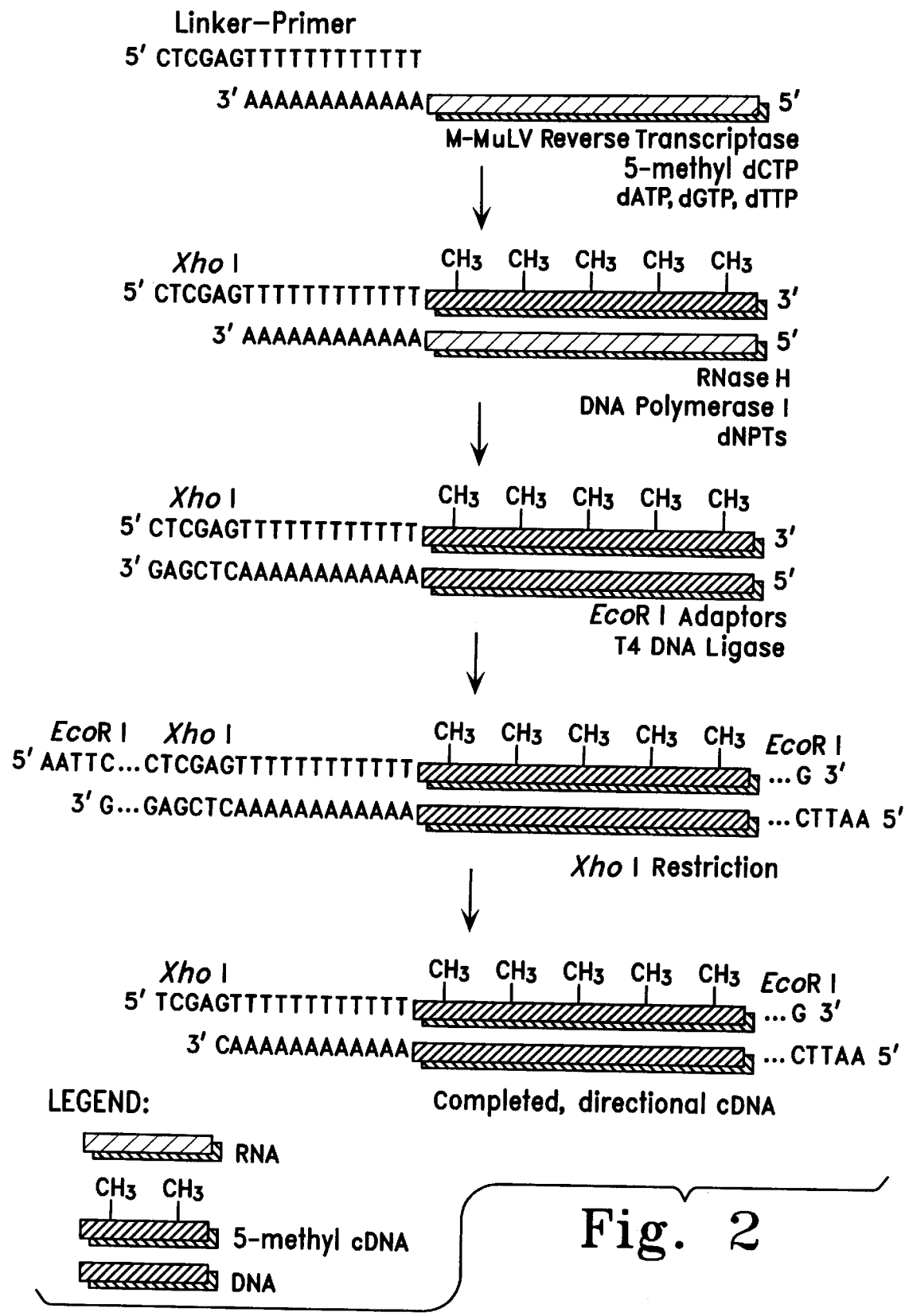
FIG. 2 is a diagram showing the details of steps of cDNA synthesis from mRNA

The composition of the buffers was as follows:
(a) 1×Binding Buffer: 10 mM Tris-HCl (pH 7.5), 0.5M LiCl, 1 mM EDTA, 0.5% LiDS;
(b) Washing Buffer with LiDS: 10 mM Tris-HCl, 0.15M LiCl, 1 mM EDTA, 0.1% LiDS Synthesis of cDNA The mRNA preparation (5 μg) isolated as above was used to synthesize cDNA using the ZAP Express® cDNA synthesis system from Stratagene (La Jolla, Calif.). The details of the steps of synthesis are presented in FIG. 2. The first strand synthesis was carried out with murine-Moloney leukemia virus reverse transcriptase (M-MuLV-RT) in the presence of mRNA, a primer containing a 50 base long oligonucleotide

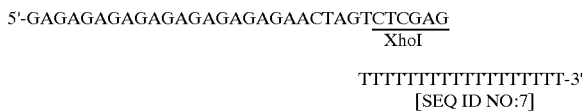

[SEQ ID NO:7]

with an XhoI restriction recognition site (shown underscored). This allows the finished cDNA to be inserted into the ZAP Express® Vector in the sense orientation (EcoRI-XhoI) with respect to the LacZ promoter. The poly (dT) region binds to the poly(A) tail of mRNA template and the reverse transcriptase starts the synthesis of first strand. The nucleotide mixture for the synthesis of first strand contained dATP, dGTP, dTTP, and 5-methyldCTP. The first strand has methyl groups on each cytosine base which protects cDNA from restriction enzymes used in subsequent cloning steps.

RNase H nicks the RNA bound to the first strand cDNA to produce multiple fragments which serve as primers for DNA polymerase I (PolI). PolI nick-translates the RNA fragments into second strand of cDNA. The cDNA ends are blunted in the presence of Klenow fragment and dNTPs. The EcoRI adaptors as shown below 5'AATTCGGCAGAG-3' [SEQ ID NO:8]
GCCGTCTCp5' are ligated to the blunt ends. The XhoI digestion of cDNA releases the EcoRI adaptor and residual linker-primer from 3'-end of the cDNA. The cDNA is size fractionated on Sephacryl-S400® and then ligated to the ZAP Express Vector® arms.

Only cDNA of 1.5 kb pairs was used to ligate into ZAP Express Vector® and then packaged into bacteriophages using Gigapack® III Gold Packaging extract protocol from Stratagene. The unamplified cDNA library generated in this way was used for subsequent screening for ACC synthase genes.

Development of a Polymerase Chain Reaction (PCR) Probe for the Screening of ACC Synthase Genes.

The first strand of cDNA synthesis was carried out with 2 μg of mRNA using the ready-to-go T-Primed First-Strand synthesis protocol obtained from Pharmacia Biotechnology (Piscataway, N.J.). The first strand cDNA product was then used to develop a PCR probe. PCR amplification (Mullis, K. B., et al, F.A. (1987), Meth. Enzymol. 155: 355–350) was performed in a Techne PHC-2 Thermocycler (Techne, Princeton, N.J.).

The following PCR primers were used:
Primer I:
  5'-GGIC/TTICCIGGITTC/TC/AGIG/ATIGG-3' [SEQ ID NO:9]
This is alternately designated as:
  5'GGNYTNCCNGGNTTYMGNRTNGG3' (where N=inosine) [SEQ ID NO:9]
Primer II:
  5'-CAIAIICG/TG/AAAG/CC/AAICCIG/AG/CC/TTC-3') [SEQ ID NO:10]
This is alternately designated as:
  5'CANANNCKRAASMANCCNRSYTC3' (where N=inosine) [SEQ ID NO:10]

The PCR reaction (50 μl) contained 5 mM Tris-HCl (pH 8.3); 3 mM MgCl$_2$, 50 mM KCl, 50 pmol of primer I: 3 μl of synthesized first strand cDNA, 200 mM each of the four dNTPs and 25 units of—(DELTA) Taq DNA polymerase (Amersham Life Sciences, Inc., Arlington Heights, Ill.). Reaction samples were overlaid with 20 μl of mineral oil. After an initial denaturation at 95° C. for 4 minutes, samples were subjected to two cycles in which conditions were 94° C. for one minute for denaturation, 60° C. for two minutes for annealing; and 72° C. for one minute for extension. It was followed by 30 cycles at 94° C. for 30 seconds; 60° C. for one minute; and 72° C. for 45 seconds. The last cycle was at 72° C. for 5 minutes.

On analysis by agarose gel electrophoresis, the amplified DNA showed a DNA band of about 360 bp. The band was localized in the gel under a UV lamp and excised. DNA from the gel was purified by using Spin-Bind Recovery system from FMC BioProducts (Rockland, Me.). The DNA was then cloned using the protocol provided by manufacturer into a TA Cloning Vector called pCRII (Invitrogen, San Diego, Calif.) and then sequenced.

The 360 bp fragment cloned in the pCRII vector was excised and used to prepare a [$^{32}$P]-labeled probe. The Maga Prime system from Amersham Life Science, Inc. (Arlington Heights, Ill.) was used according to the manufacturer's protocol. The labeled DNA probe incorporated nearly 70% of the input [α$^{32}$P]dATP.

Isolation of cDNA clones from the cDNA library

Unamplified recombinant bacteriophages (1×10$^6$ pfu) were screened with the [$^{32}$P]labeled probe. Phages (50,000 pfu) were grown on a 150-mm NZY plate for six hours at 37° C. The plates were cooled to 4° C. Phages were transferred onto a Hybond-N+ nylon membrane (Amersham, Inc.) for 40 seconds. The DNA on membrane was denatured by treatment with 1.5M NaCl–0.5M NaOH for 2 minutes, neutralized in 1.5M NaCl–0.5M Tris-HCl (pH 8.0) for 5 minutes and finally washed 0.2M Tris-HCl (pH 7.5), 2×SSC for 30 seconds. DNA was fixed onto the membrane by UV cross-linking (Strategene UV Cross-Linker) and then baked at 80° C. for one hour.

The membrane was treated with Rapid-hyb® buffer (Amersham, Inc.) at 55° C. for one hour for prehybridization and then probed with [$^{32}$P]-labeled PCR probe for 3 hours at 55° C. The membranes were washed with 2×SSC-0.1% SDS for one hour at room temperature and with 0.2-×SSC-0.1% SDS at room temperature. The filters were then exposed to X ray film (Fuji).

A total of 95 putative clones were identified during the first screening of the cDNA library. Of these putative clones, 24 were further screened in the second screening cycle at lower density (1000–4000 pfu). Nine putative clones from the second screening were subjected to a tertiary screening. All these nine clones showed strong signal and were judged to be positive.

These clones were in vivo excised out of the pBK-CMV phagemid vector, and the size of the cDNA insert (representing ACC synthase genes) was determined by electrophoresis. Clones were judged to be nearly full-length, as confirmed by subsequent DNA sequencing.

DNA Sequencing of Clones

The dideoxy chain termination method (Sanger, F., et al., (1977), *Proc. Natl. Acad. Sci. USA* 74: 5463–5467)) was used to sequence the ACC synthase cDNA clones. This method employed the DELTA Taq DNA polymerase protocol developed in the present inventor's laboratory (Ranu, R. S., (1995), *Biotechniques* 18: 390–395) or Thermo Sequenase® (Amersham, Inc.). Based on the analysis of the DNA sequence results, the ACC synthase cDNA clones were classified into three classes belonging to two groups:

Group I

Class 1: pPHSacc41 [SEQ ID NO:1] was 1945 bp in length with an open reading frame (ORF) of 1446 encoding a polypeptide of 52.2 kDa Class 2: pPHSacc44 [SEQ ID NO:2] was 2678 bp in length with an ORF of 1446 bp encoding a 54.2 kDa;

Group II

Class 3: pPHSacc49 [SEQ ID NO:3] was 1893 bp in length with an ORF of 1470 bp encoding a 55.1 kDa polypeptide.

All three of the above clones were full-length. Based sequence homologies of the ORF, class 1and 2 were grouped as Group I and class 3 as Group II. Groups I and II had 58% nucleotide sequence similarity and the deduced amino acid sequence [SEQ ID NO: 4, 5 and 6, respectively] showed 67% similarity. The DNA sequences of these clones are shown in FIGS. 3–5. These figures also show various landmarks, including start codon, termination signal and polyA- signal. The deduced amino acid sequences are shown in FIGS. 6–8.

Clone pPHSacc44 was unusual in several respects. First, it is 780 bp longer than clone 41. Second it has two distinct poly A signal sequences and polyA "tails" separated by 780 bases of 3' regulatory sequence which are present in genomic DNA. Thus, clone pPHSacc44 appears to include two separate regulatory regions 3' from coding sequence.

Several additional features of these clones and several related clones which include some noteworthy areas as described below. Group I clones included a stop codon (TAG) just before the first AUG codon; the group II clone had a stop codon (TGA) 21 bp upstream of the first AUG. Clone pPHSacc44 had an "extra" 780 bp after a first short (22 bp) 3'-poly(A) tail. Both the poly(A) signal and poly(A) tail were present twice, at the normal 3' untranslated region (3'UTR) and in the extra 3'UTR.

Development of Antibody Probes

Antibody probes were prepared for screening a cDNA expression library and for subsequent detection of ACC synthase gene products from plant cell extracts and for protein expressed from the cloned ACC synthase DNA. Based on the sequence alignment data from tomato, three peptides with largest stretches of amino acid sequence homology were selected.

(1) Peptide #1075, derived from the carboxy-terminus contained 35 amino acid residues as follows:
    N V S P G S S F L C S E P G W F R V C F A N M D - NATLDVALNRI [SEQ ID NO:11]

(2) Peptide #1076, derived from the amino terminus contained 33 amino acids as follows:

Y F D G W K A Y D R D P Y H S T K N - SNGVIQMGLAENQLC [SEQ ID NO:12]

(3) Peptide #1077, from the middle region contained 38 amino acid residues as follows:
    Y S L S K D M G M P G F R V G I I Y S Y N D R V V S - TARRMSSFGLVS [SEQ ID NO:13]

These peptides were used to immunize rabbits. A 1:1 emulsion of 200 μg/ml of peptide in complete Freund's Adjuvant was prepared, and 0.1 ml volumes were injected subcutaneously (sc) into three different rabbits at 17 to 18 sites on the animals' backs. Before injection, a preimmune serum sample was obtained. On day 19 after the first immunization, rabbits received two intramuscular (im) injections of 0.35 ml of a 1:1 emulsion of each peptide in incomplete Freund's adjuvant at 100 μg/ml. On day 35 after the first immunization, the day 19 im protocol was repeated. On day 92, each rabbit received a booster injection (im) with the same peptide emulsion as on day 19. Seven days later, the rabbits were bled, and serum was prepared.

Western blot analysis of antisera with the three peptides showed the presence of antibodies against each of the three peptides and strong signals indicating immunization was successful. Preimmune sera were negative.

Expression of Cloned ACC Synthase Genes In Vitro

Use was made of the ZAP Express Vector system which contains a bacteriophage $T_3$ promoter. Cloned ACC synthase genes are inserted by unidirectional EcoRI/XhoI site. The cloned insert can be excised from the phage in the form of a kanamycin-resistant pBK-CMV phagemid. The digestion of the phagemid from the three ACC synthase clones described above with NotI and BamI restriction enzymes showed the absence of these restriction sites in the inserts.

DNA from clones pPHSacc 41, pPHSacc 44 and pPHSacc49 was prepared, linearized with NotI and used for in vitro transcription. The reaction mixture (100 μl) contained Tris-HCl (pH7.9), 40 mM; $MgCl_2$, 6 mM; DTT, 10 mM; spermidine, 2 mM; $m^7$GpppG, 1 mM; ATP, CTP and UTP, 0.5 mM each; GTP, 25 μM; Rnasin® (RNase inhibitor), 120 units; DNA template, 1–2 μg; and $T_3$ RNA polymerase, 50 units, as described in the inventor's publications. Samples were incubated at 37° C. for 20 minutes. The GTP concentration in reaction mixture was raised to 0.5 mM, and incubation was continued for one hour. Aliquots (3–5 μl) of each reaction mixture were withdrawn and subjected to agarose gel (1.2%) electrophoresis to determine the quality and efficiency of transcript synthesis. The analysis of transcript showed expected size of RNA from each clone.

The in vitro transcripts from each clone were then translated at high efficiency using rabbit reticulocyte lysates as described by the present inventor (Ranu, R. S., et al, 1979, *Meth. Enzymol.* 60: 459–484) except that they were made mRNA-dependent by treatment with micrococcal ribonuclease. The in vitro translation products were immunoprecipitated with each of the three antisera described above or with a mixture of the antisera. The method used for immunoprecipitation and detection of ACC synthase protein was by Western blotting as described by the present inventor and colleagues in 1989 and recently published (Ranu, R. S., et al, (1996) *Gene Expression* 5: 143–153). Translation products detected from each cloned ACC synthase gene was the size expected based on the size of the ORF of each clone. The in vitro translation product comigrate with the in vivo product upon gel electrophoresis.

The results described above are consistent with those obtained in other plant species indicating that the geranium ACC synthase genes belong to a multigene family. Despite the fact that these genes contain a termination codon immediately 5' to the initiation codon (in clones pPHSacc41 and pPHSacc44 ), or 21 nucleotides upstream from the initiation codon (clone pPHSacc49), the transcripts produced from these DNA sequences were translated efficiently in vitro. Clones pPHSacc44 and pPHSacc41 differ from each other in clone 44 contains an extra 780 bases of 3'UTR which has a profound effect on translation of the transcript, reducing the translation dramatically. These results suggest a regulatory role for the 3'UTR in the expression of this gene.

The references cited above are all incorporated by reference herein, whether specifically stated as incorporated or not. Specifically, any references mentioned in the application for this patent as well as all references listed in any information disclosure originally filed with the application are hereby incorporated by reference in their entirety to the extent such may be deemed essential to support the enablement of the invention(s), however, applicant disclaims making or supporting any statements in said references which might be considered inconsistent with the patentability of the following claims or any aspect of the invention described.

Having now fully described this invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This patent covers any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims. Further, it should be understood that various permutations and combination of the elements shown in the claims (whether method or apparatus) are possible and do fall within the scope of this disclosure.

DEPOSITS

The following illustrative plasmids encoding geranium ACC synthase were deposited at the American Type Culture Collection, Rockville, Md., prior to the filing date of this patent under the requirements of the Budapest Treaty. These deposits were granted the following accession numbers and are hereby incorporated by reference:

1. pPHSacc41 cDNA clone comprising SEQ ID NO:1— accession number ATCC 98177;
2. pPHSacc44 cDNA clone comprising SEQ ID NO:2— accession number ATCC 98178; and
3. pPHSacc49 cDNA clone comprising SEQ ID NO:3— accession number ATCC 98179.

What is claimed is:

1. An isolated DNA molecule consisting of SEQ ID NO:1.
2. An isolated DNA molecule consisting of SEQ ID NO:2.
3. An isolated DNA molecule consisting of SEQ ID NO:3.
4. An isolated DNA molecule encoding an ACC synthase enzyme of geranium which DNA molecule hybridizes under high stringency conditions with SEQ ID NO:1.
5. An isolated DNA molecule encoding an ACC synthase enzyme of geranium which DNA molecule hybridizes under high stringency conditions with SEQ ID NO:2.
6. An isolated DNA molecule encoding an ACC synthase enzyme of geranium which DNA molecule hybridizes under high stringency conditions with SEQ ID NO:3.
7. A vector useful when introduced into a geranium plant cell, comprising an oligonucleotide or polynucleotide which is complementary to the nucleotide sequence SEQ ID NO:1 or is complementary to an RNA sequence encoded by SEQ ID NO:1.
8. A vector useful when introduced into a geranium plant cell, comprising an oligonucleotide or polynucleotide which is complementary to the nucleotide sequence SEQ ID NO:2 or is complementary to an RNA sequence encoded by SEQ ID NO:2.
9. A vector useful when introduced into a geranium plant cell, comprising an oligonucleotide or polynucleotide which is complementary to the nucleotide sequence SEQ ID NO:3 or is complementary to an RNA sequence encoded by SEQ ID NO:3.
10. A vector useful when introduced into a geranium plant cell, comprising an oligonucleotide or polynucleotide which is complementary to a nucleotide sequence which encodes an ACC synthase enzyme of geranium and which hybridizes under high stringency conditions with the nucleotide sequence SEQ ID NO:1 or is complementary to an RNA sequence encoded by such nucleotide sequence.
11. A vector useful when introduced into a geranium plant cell, comprising an oligonucleotide or polynucleotide which is complementary to a nucleotide sequence which encodes an ACC synthase enzyme of geranium and which hybridizes under high stringency conditions with the nucleotide sequence SEQ ID NO:2 or is complementary to an RNA sequence encoded by such nucleotide sequence.
12. A vector useful when introduced into a geranium plant cell, comprising an oligonucleotide or polynucleotide which is complementary to a nucleotide sequence which encodes an ACC synthase enzyme of geranium and which hybridizes under high stringency conditions with the nucleotide sequence SEQ ID NO:3 or is complementary to an RNA sequence encoded by such nucleotide sequence.
13. A vector according to claim 7, 8, 9, 10, 11, or 12 and further comprising regulatory sequences required for expression of said oligonucleotide or polynucleotide in said cell.
14. A vector according to claim 13 wherein said regulatory sequences comprise a promoter active in said cell.
15. A vector according to claim 14, wherein said regulatory sequences further comprise a polyadenylation signal.
16. A vector according to claim 14, wherein said promoter comprises a heterologous promoter.
17. A vector according to claim 14, wherein said heterologous promoter is a viral promoter.
18. A vector according to claim 17, wherein said viral promoter is the CaMV 35S promoter or a promoter homologous to CaMV35S.
19. A vector according to claim 16, wherein said heterologous promoter is selected from the group consisting of the SSU gene promoter, ribulose bisphosphate carboxylase promoter, chlorophyll a/b binding protein promoter, potato ST-LS1 gene promoter, soybean heat shock protein hsp17.5-E promoter, soybean heat shock protein hsp17.3-B promoter, phenylalanine ammonia-lyase promoter, petunia 5-enolpyruvylshikimate-3-phosphate synthase gene promoter, *Rhizobium meliloti* FIXD gene promoter and nopaline synthase promoter.
20. A geranium cell transformed with a vector according to claim 7, 8, 9, 10, 11, or 12.
21. A mature geranium plant regenerated from a cell transformed with a vector according to claim 7, 8, 9, 10, 11, or 12.
22. A plant part of a geranium plant according to claim 21.
23. An isolated nucleic acid molecule encoding an amino acid sequence consisting of SEQ ID NO:4.
24. An isolated nucleic acid molecule encoding an amino acid sequence consisting of SEQ ID NO:5.
25. An isolated nucleic acid molecule encoding an amino acid sequence consisting of SEQ ID NO:6.

* * * * *